United States Patent
Leavitt et al.

(10) Patent No.: US 11,000,229 B2
(45) Date of Patent: May 11, 2021

(54) SYSTEMS, METHODS, AND APPARATUSES FOR INTEGRATING A BODY JOINT REHABILITATION REGIMEN WITH A WEARABLE MOVEMENT CAPTURE DEVICE OPERABLE IN CONJUNCTION WITH A CLOUD BASED COMPUTING ENVIRONMENT

(71) Applicant: Orthini, LLC, Portland, OR (US)

(72) Inventors: Mark Leavitt, North Plains, OR (US); LaJean Lawson, Portland, OR (US); Chris Nanson, Tualatin, OR (US)

(73) Assignee: Orthini, LLC, Portland, OR (US)

( * ) Notice: Subject to any disclaimer, the term of this patent is extended or adjusted under 35 U.S.C. 154(b) by 350 days.

(21) Appl. No.: 16/054,956

(22) Filed: Aug. 3, 2018

(65) Prior Publication Data

US 2019/0038225 A1 Feb. 7, 2019

Related U.S. Application Data

(60) Provisional application No. 62/540,967, filed on Aug. 3, 2017.

(51) Int. Cl.
*A61B 5/00* (2006.01)
*A61B 5/11* (2006.01)
(Continued)

(52) U.S. Cl.
CPC .......... *A61B 5/6831* (2013.01); *A61B 5/0022* (2013.01); *A61B 5/1122* (2013.01);
(Continued)

(58) Field of Classification Search
None
See application file for complete search history.

(56) References Cited

U.S. PATENT DOCUMENTS 6,428,490 B1 * 8/2002 Kramer ............... A61B 5/1071
600/595
2010/0286950 A1 * 11/2010 Heijkants ............ A61B 5/6828
702/151

(Continued)

FOREIGN PATENT DOCUMENTS

EP 2057944 A1 5/2009

*Primary Examiner* — Rene T Towa
*Assistant Examiner* — Benjamin S Melhus
(74) *Attorney, Agent, or Firm* — Elliott, Ostrander & Preston, P.C

(57) ABSTRACT

In accordance with disclosed embodiments, there are provided systems, methods, and apparatuses for integrating a body joint rehabilitation regimen with a wearable movement capture device operable in conjunction with a cloud based computing environment. For instance, a wearable apparatus for monitoring activity of a body joint such as knee or elbow for monitoring rehabilitation and recovery after surgical procedures and after injury to the joint is disclosed. Such a wearable apparatus includes a wearable harness in which a first portion of the wearable harness includes an proximal strap to be positioned proximal to the body joint and in which a second portion of the wearable harness includes a distal strap to be positioned distal to the body joint, in which the wearable harness is positionable upon a patient's body at the body joint without occluding a surgical site of the patient. Such a wearable harness further includes a connecting section having a first end connected with the proximal strap and a second end connected with the distal strap and a first buckle housing (smart buckle) secured to the proximal strap of the wearable harness and a second buckle housing secured to the distal strap of the wearable harness, in which the proximal and distal straps maintain the first and the second buckles in a consistent position relative to the axis of an underlying bone such as a thigh bone, calf bone, femur, or tibia of a patient. The wearable harness further includes (Continued)

integrated circuitry including at least a magnetometer and accelerometer within the first buckle and an accelerometer within the second buckle. A microprocessor of the smart buckle periodically reads a switch position on the buckles, reads the magnetometer and accelerometer data and processes the data to determine (i) an angle for the sample period, and periodically classify an activity (e.g., as walking, standing, sitting, elevating, and icing, etc.). Such data is relayed to a cloud computing environment for further analysis and for access by clinicians and patients. Other related embodiments are disclosed.

22 Claims, 17 Drawing Sheets

(51) Int. Cl.
*G16H 80/00* (2018.01)
*G16H 10/60* (2018.01)
*G16H 20/30* (2018.01)
*G16H 40/67* (2018.01)
*A61B 5/107* (2006.01)

(52) U.S. Cl.
CPC .......... *A61B 5/4528* (2013.01); *A61B 5/4533* (2013.01); *G16H 10/60* (2018.01); *G16H 20/30* (2018.01); *G16H 40/67* (2018.01); *G16H 80/00* (2018.01); *A61B 5/1071* (2013.01); *A61B 5/112* (2013.01); *A61B 5/1123* (2013.01); *A61B 5/458* (2013.01); *A61B 5/4585* (2013.01); *A61B 5/6824* (2013.01); *A61B 5/6828* (2013.01); *A61B 5/6829* (2013.01); *A61B 2505/09* (2013.01); *A61B 2562/0219* (2013.01); *A61B 2562/0223* (2013.01)

(56) References Cited

U.S. PATENT DOCUMENTS

| | | | |
|---|---|---|---|
| 2012/0143093 A1* | 6/2012 | Stirling | A61B 5/6804 600/592 |
| 2013/0217998 A1* | 8/2013 | Mahfouz | A61B 5/11 600/409 |
| 2014/0114453 A1* | 4/2014 | Bentley | A63B 69/3632 700/91 |
| 2015/0302162 A1* | 10/2015 | Hughes | G09B 19/0038 702/19 |
| 2016/0089571 A1* | 3/2016 | Wesley | A61B 5/4528 482/8 |
| 2016/0220175 A1* | 8/2016 | Tam | A61B 5/1127 |
| 2016/0302721 A1 | 10/2016 | Wiedenhoefer et al. | |
| 2016/0361014 A1 | 12/2016 | Kane et al. | |
| 2018/0093121 A1* | 4/2018 | Matsuura | A63B 21/00185 |
| 2020/0174517 A1* | 6/2020 | Martinez | A61B 5/6831 |

* cited by examiner

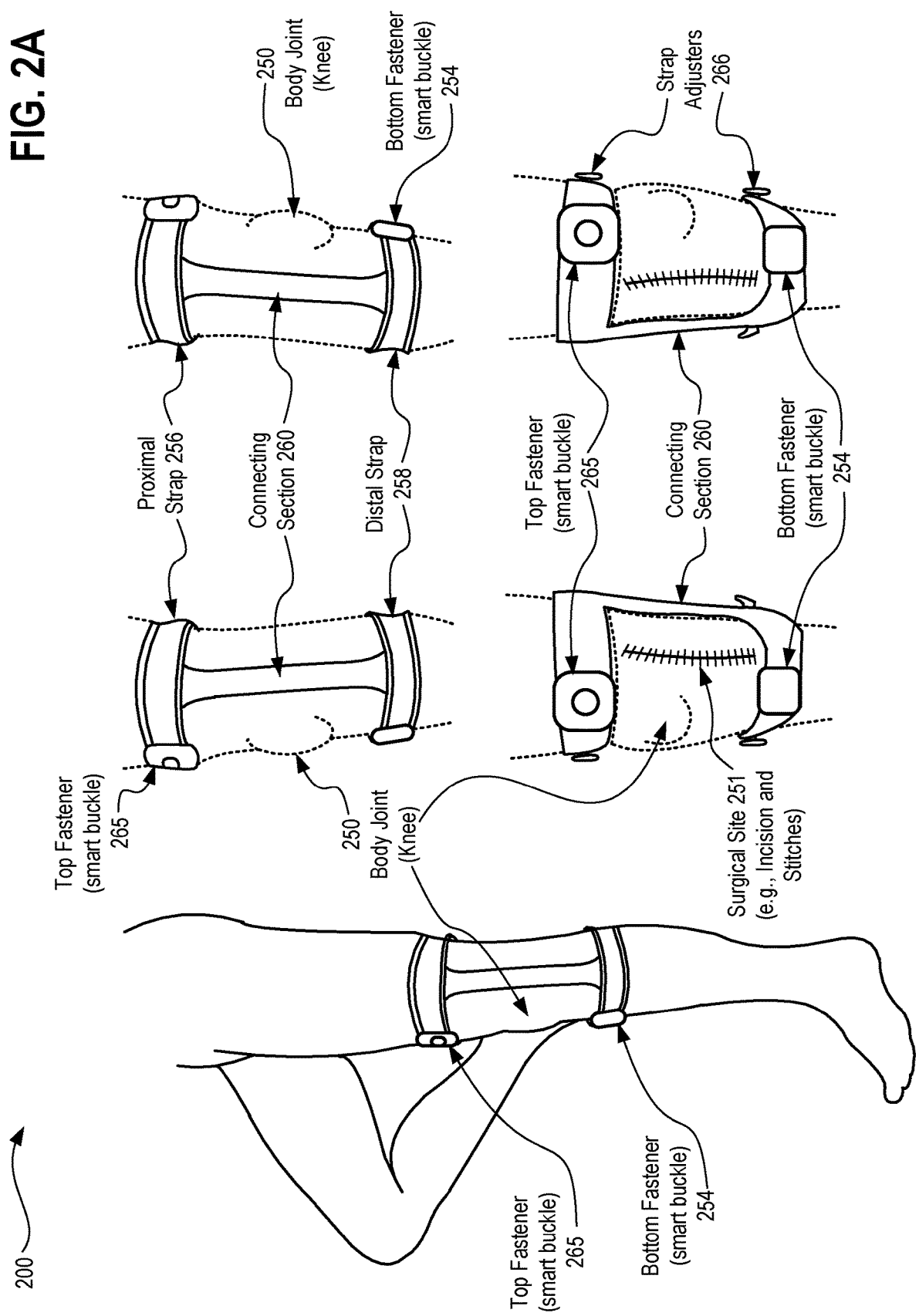

SYSTEMS, METHODS, AND APPARATUSES FOR INTEGRATING A BODY JOINT REHABILITATION REGIMEN WITH A WEARABLE MOVEMENT CAPTURE DEVICE OPERABLE IN CONJUNCTION WITH A CLOUD BASED COMPUTING ENVIRONMENT

CLAIM OF PRIORITY

This U.S. utility non-provisional patent application is related to, and claims priority to the U.S. provisional utility application entitled "BODY JOINT REHABILITATION SYSTEMS, DEVICES, AND METHODS," filed on Aug. 3, 2017, having an application number of 62/540,967, the entire contents of which are incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments disclosed herein relate generally to the field of computing and medical devices, and more particularly, to systems, methods, and apparatuses for integrating a body joint rehabilitation regimen with a wearable movement capture device which is operable in conjunction with a cloud based computing environment such as a database system implementation supported by a processor and a memory to execute such functionality. Such means may be implemented within the computing architecture of a hosted computing environment, such as an on-demand or cloud computing environment hosted database technologies, client-server technologies, local server side dedicated database technologies or other computing architecture in support of the hosted computing environment capable of collecting, storing, and reporting movement capture data.

BACKGROUND

The subject matter discussed in the background section is not to be assumed as prior art merely as a result of its mention in the background section. Similarly, a problem mentioned in the background section or associated with the subject matter of the background section is not assumed to have been previously recognized in the prior art. The subject matter in the background section merely represents different approaches, which in and of themselves may also correspond to claimed embodiments.

It is well known that human bodies are susceptible to injury and wear over time, especially within their body joints, such as the knees, shoulders, elbows, and hips. Rehabilitation needs may relate to increased aging, obesity, and sports-related injuries, for example. When such individuals encounter joint pain, they may seek out the assistance of medical doctors, surgeons, physical therapists, in an effort to alleviate pain and improve use of their body joints.

Medical treatment of such joints may include directed exercise, motion, or usage, which may in some instances be undertaken alone and in other instances, may include surgical or other medical treatment at or in the vicinity of the joint. For example, surgical procedures for treatment of body joints may include replacement or reconstruction of a joint or proximal or associated tissue to the joint.

Regardless of the treatment, successful joint rehabilitation has been demonstrably correlated to patient cooperation and compliance with prescribed rehabilitation exercises, treatments, and so forth. For instance, subsequent to surgical replacement or reconstruction of a body joint, the patient may be prescribed with a body joint rehabilitation regimen which includes medically prescribed movements, medically prescribed durations of rest or exercise, medically prescribed intervals of icing, and so forth.

Improved patient compliance with such prescribed body joint rehabilitation regimens will aid the patients with improved recovery times, possibly facilitate greater recovery of use of the treated body joint, and may additionally alleviate medical expense pressures for the patient and medical insurance industry owing to decreased hospital length-of-stay and/or reduced physical therapy encounters.

Unfortunately, patient compliance with a prescribed rehabilitation regimen often falls directly on a patient who must self-report compliance or a lack of compliance, as well as self-report efficacy of the treatment, post-operative pain levels, degrees of movement attained over time subsequent to treatment, and so forth. Such dependence upon the patient is simply not effective. Consequently, there is a need for more efficient, more effective, and less costly monitoring of patients undergoing body joint rehabilitation.

The present state of the art may therefore benefit from the systems, methods, and apparatuses for integrating a body joint rehabilitation regimen with a wearable movement capture device operable in conjunction with a cloud based computing environment as is described herein.

BRIEF DESCRIPTION OF THE DRAWINGS

Embodiments are illustrated by way of example, and not by way of limitation, and will be more fully understood with reference to the following detailed description when considered in connection with the figures in which:

FIG. 2A depicts multiple views of a wearable harness embodying the wearable patient device in accordance with described embodiments;

DETAILED DESCRIPTION

Figure 1A:
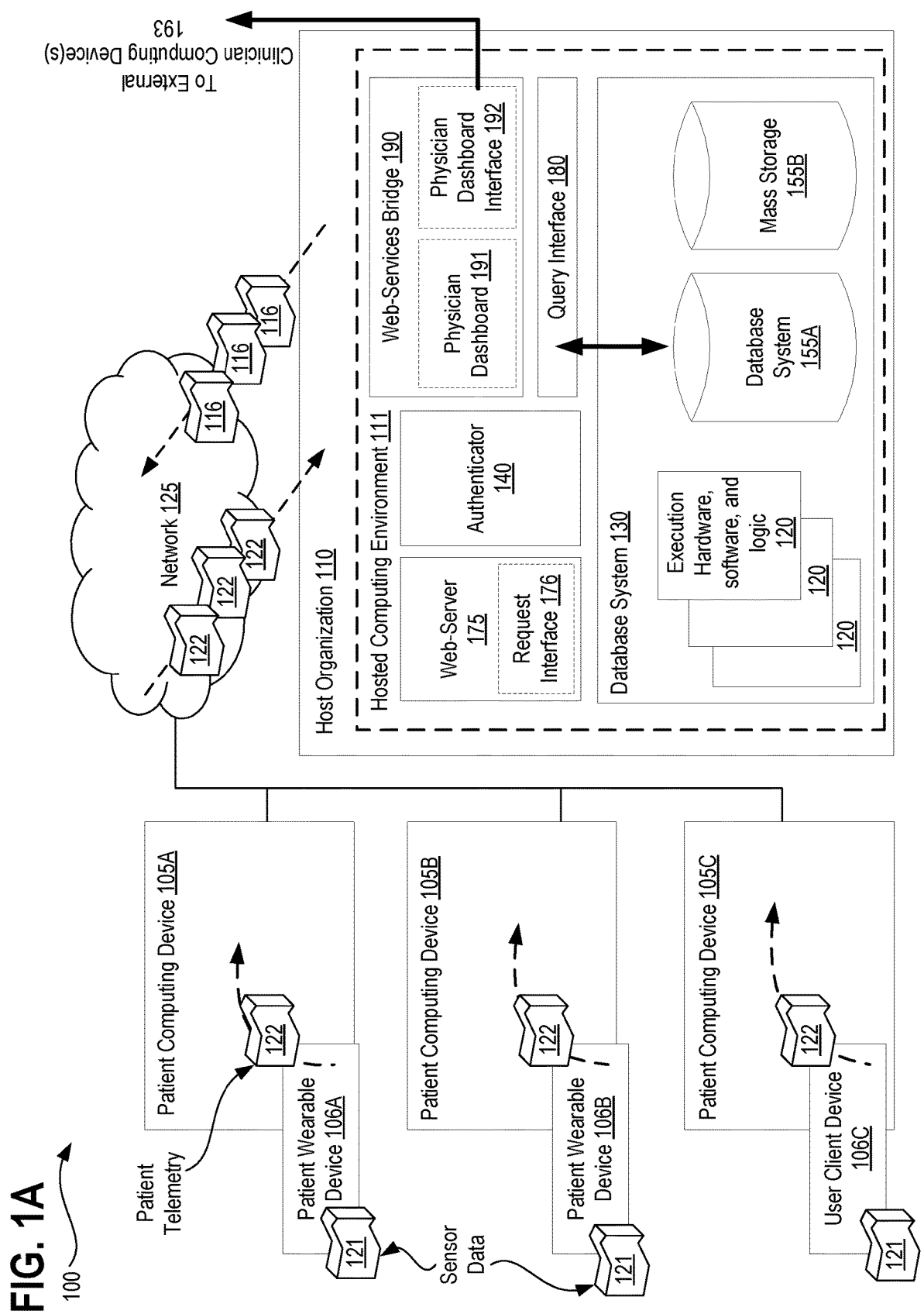
FIG. 1A depicts an exemplary architecture in accordance with described embodiments.

Described herein are systems, methods, and apparatuses for integrating a body joint rehabilitation regimen with a wearable movement capture device which is operable in conjunction with a cloud based computing environment. For instance, a wearable apparatus for monitoring activity of a body joint such as knee or elbow for monitoring rehabilitation and recovery after surgical procedures and after injury to the joint is disclosed. Such a wearable apparatus includes a wearable harness in which a first portion of the wearable harness includes a proximal strap to be positioned proximal to the body joint and in which a second portion of the wearable harness includes a distal strap to be positioned distal to the body joint, in which the wearable harness is positionable upon a patient's body at the body joint without occluding a surgical site of the patient. Such a wearable harness further includes a connecting section having a first end connected with the proximal strap and a second end connected with the distal strap and a first buckle housing (smart buckle) secured to the proximal strap of the wearable harness and a second buckle housing secured to the distal strap of the wearable harness, in which the proximal and distal straps maintain the first and the second buckles in a consistent position relative to the axis of an underlying bone such as a thigh bone, calf bone, femur, or tibia of a patient. The wearable harness further includes integrated circuitry including at least a magnetometer and accelerometer within the first buckle and an accelerometer within the second buckle. A microprocessor of the smart buckle periodically reads a switch position on the buckles, reads the magnetometer and accelerometer data and processes the data to determine (i) an angle for the sample period, and periodically classify an activity (e.g., as walking, standing, sitting, elevating, and icing, etc.). Such data is relayed to a cloud computing environment for further analysis and for access by clinicians and patients.

There is a rapidly growing demand for joint replacement surgeries, driven by aging, obesity, and sports-related injuries, etc. Outcomes are strongly dependent on patient cooperation and compliance during post-operative rehabilitation and there are powerful cost pressures to decrease hospital length-of-stay (e.g. day surgery) and reduce physical therapy encounters (e.g. bundled payments). A more efficient, more effective, less costly means of monitoring and rehabilitating patients after joint replacement is needed.

The underlying principle of functional monitoring includes Rubor, calor, dolor, tumor (redness, heat, pain, swelling), sometimes known as the four cardinal signs of inflammation. Functio laesa (loss of function) represents the fifth sign of inflammation. Loss of function is a sensitive indicator of post-operative complications as well as degree of rehabilitation following joint surgery. The wearable harness developed by Orthini bases its post-operative monitoring on joint function—both static (range of motion) and dynamic (activities undertaken)—as well as the timely, progressive improvement of these measurements.

Cryotherapy Monitoring is principled on the basis that Cryotherapy (cold therapy) is a traditional mainstay of treatment to reduce swelling, inflammation, and pain. Patient compliance with cryotherapy is often incomplete or absent. The wearable harness and complementary system developed by Orthini provides the correct size and capacity of cold therapy for the operative site, and encourages timely, consistent applications by electronically monitoring its use. Moreover, the Orthini System encourages patients to exercise immediately following cryotherapy. Such coordination takes advantage of the temporary pain relief of cryotherapy to increase range of motion and strength.

In the following description, numerous specific details are set forth such as examples of specific systems, languages, components, etc., in order to provide a thorough understanding of the various embodiments. It will be apparent, however, to one skilled in the art that these specific details need not be employed to practice the embodiments disclosed herein. In other instances, well known materials or methods have not been described in detail in order to avoid unnecessarily obscuring the disclosed embodiments.

In addition to various hardware components depicted in the figures and described herein, embodiments further include various operations which are described below. The operations described in accordance with such embodiments may be performed by hardware components or may be embodied in machine-executable instructions, which may be used to cause a special-purpose processor programmed with the instructions to perform the operations. Alternatively, the operations may be performed by a combination of hardware and software.

Embodiments also relate to an apparatus for performing the operations disclosed herein. This apparatus may be specially constructed for the required purposes, or it may utilize specially configured computing components which are selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various special purpose systems may be used with programs in accordance with the teachings herein, or it may prove convenient to construct more specialized apparatus to perform the required method steps. The required structure for a variety of these systems will appear as set forth in the description below. In addition, embodiments are not described with reference to any particular programming language. It will be appreciated that a variety of programming languages may be used to implement the teachings of the embodiments as described herein.

Embodiments may be provided as a computer program product, or software, that may include a machine-readable medium having stored thereon instructions, which may be used to program a computer system (or other electronic devices) to perform a process according to the disclosed embodiments. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical), etc.

Any of the disclosed embodiments may be used alone or together with one another in any combination. Although various embodiments may have been partially motivated by deficiencies with conventional techniques and approaches, some of which are described or alluded to within the specification, the embodiments need not necessarily address or solve any of these deficiencies, but rather, may address only some of the deficiencies, address none of the deficiencies, or be directed toward different deficiencies and problems which are not directly discussed.

FIG. 1A depicts an exemplary architecture 100 in accordance with described embodiments. In one embodiment, a hosted computing environment 111 is communicably interfaced with a plurality of patient computing devices 105A-C (e.g., such as mobile devices, smart phones, tablets, PCs, etc.) through host organization 110. In one embodiment, a database system 130 includes databases 155A and mass storage 155B devices, for example, to store application code, object data, tables, datasets, and underlying database records with user and patient telemetry 122 data on behalf of both the patient computing devices and the external clinician computing devices 193 (e.g., users and patients prescribed the patient wearable device 106A-C or doctors, nurses, medical practitioners and clinicians who may reference the patient telemetry 122 data stored within the database system 130). Such databases 155A may include various database system types including, for example, a relational database system 155A and a non-relational database system or the mass storage device 155B as depicted here, according to certain embodiments.

In certain embodiments, a client-server computing architecture may be utilized to supplement features, functionality, or computing resources for the database system 130 or alternatively, a computing grid, or a pool of work servers, or some combination of hosted computing architectures may be utilized to carry out the computational workload and processing demanded of the host organization 110 in conjunction with the database system 130.

Further depicted are the patient wearable devices 106A-C which are communicably interfaced to the patient computing devices 105A-C. The patient wearable devices 106A-C receive, generate, and collect sensor data 121 from the various sensors integrated within the patient wearable devices 106A-C and communicate telemetry data 122 from the patient wearable devices 106A-C to the patient computing device 105A-C via a local wireless communications interface such as WiFi or Bluetooth, etc. In alternative embodiments, the patient wearable devices 106A-C may be configured with an integrated cellular or wireless communications device such as LTE, 3G, 4G, 5G communications integrated circuits which then allow the patient wearable devices 106A-C to communicate patient telemetry 122 data directly with the host organization 110 via network 125, thus bypassing the patient computing devices 105A-C. However, as depicted here, the patient wearable devices 106A-C communicate the patient telemetry 122 data to the patient computing devices 105A-C which then in turn forward, relay, or responsively communicate such patient telemetry data 122 to the host organization 110 via network 125 where it is then stored by the database system 130 and made accessible to the external clinician computing devices 193 via the physician dashboard 191 and physician dashboard interface 192.

The database system 130 depicted in the embodiment shown includes a plurality of underlying hardware, software, and logic elements 120 that implement database functionality and a code execution environment within the host organization 110.

In accordance with one embodiment, database system 130 utilizes the underlying database system implementations 155A and mass storage devices 155B to service database queries and other data interactions with the database system 130 which communicate with the database system 130 via the query interface. The hardware, software, and logic elements 120 of the database system 130 are separate and distinct from the patient computing devices 105A-C and the external clinician computing devices 193 which may ultimately reference the stored patient telemetry data 122 stored by the database system 130 via the respective request interface 176 and web-server 175 functions of the host organization. For instance, as depicted here, the plurality of patient computing devices (105A, 105B, and 105C) utilize web services and other service offerings as provided by the host organization 110 by communicably interfacing to the host organization 110 via network 125. In such a way, host organization 110 may implement on-demand services, on-demand database services or cloud computing services to subscribing customer organizations 105A-C and to the external clinician computing devices 193, each of which leverage the cloud based repository and computing functionality of the host organization 110. In alternative embodiments, it is feasible for the external clinician computing devices 193 to host and store the database technology necessary to provide such services, however, it is preferred that such data be stored by a cloud based host organization so as to reduce the complexity of implementation for both the external clinician computing devices 193 and the patient computing devices 105A-C which may then simply utilized the provided technologies of the host organization 110 as a service.

Further depicted is the host organization 110 receiving input and other requests from a plurality of patient computing devices organizations 105A-C via network 125 (such as a public Internet), including the receipt of incoming patient elementary data 122. Additionally, incoming search queries, database queries, API requests, interactions with displayed graphical user interfaces and displays at the patient computing devices 105A-C and the external clinician computing devices 193 may be transmitted to the host organization 110 for processing against the database system 130, or alternatively, such queries may be constructed from the inputs and other requests 115 for execution against the database 155A and mass storage device 155B or the query interface 180, pursuant to which results 116 are then returned to an originator or requestor, such as a user of one of a patient computing devices 105A-C or one of the external clinician computing devices 193.

In one embodiment, patient telemetry data 122 is received and stored by the host organization 110, subsequent to which application requests (e.g., from an application executing at the patient computing devices 105A-C or one of the external clinician computing devices 193) are received at, or submitted to, a web-server 175 within host organization 110. Host organization 110 may receive a variety of requests for processing by the host organization 110 and its database system 130. Incoming patient telemetry data 122 and subsequent requests received at web-server 175 may specify which services from the host organization 110 are to be provided, such as query requests, search request, status requests, database transactions, graphical user interface requests and interactions, processing requests to retrieve, update, or store data on behalf of one of the patient computing devices 105A-C, code execution requests, and so forth. Web-server 175 may be responsible for receiving such telemetry data 122 and requests from various patient computing devices 105A-C via network 125 on behalf of the query interface 180 and for providing a web-based interface or other graphical displays to an end-user at a patient computing devices 105A-C or one of the external clinician computing devices 193 or another machine originating such data requests.

The query interface 180 is capable of receiving and executing requested queries against the databases and storage components of the database system 130 so as to return a result set, response, or other requested data in furtherance of the methodologies described. The query interface 180 additionally provides functionality to pass queries from web-server 175 into the database system 130 for execution against the databases 155 for processing search queries, or into the other available data stores of the host organization's computing environment 111. In one embodiment, the query interface 180 implements an Application Programming Interface (API) through which queries may be executed against the databases 155A or the other data stores, such as the mass storage device 155B.

Host organization 110 may implement a request interface 176 via web-server 175 or as a stand-alone interface to receive requests packets, incoming patient telemetry data 122 other requests from the patient computing devices 105A-C. Request interface 176 further supports the return of response packets or other replies and responses 116 in an outgoing direction from host organization 110 to the patient computing devices 105A-C and to the external clinician computing devices 193.

Authenticator 140 operates on behalf of the host organization to verify, authenticate, and otherwise credential users attempting to gain access to the host organization.

Still further depicted within the hosted computing environment 111 is the web-services bridge 190 having therein both a physician dashboard 191 and also a physician dashboard interface 192 (also referred to as a clinician interface) capable of communicating with the external clinician computing devices 193.

Figure 1B:
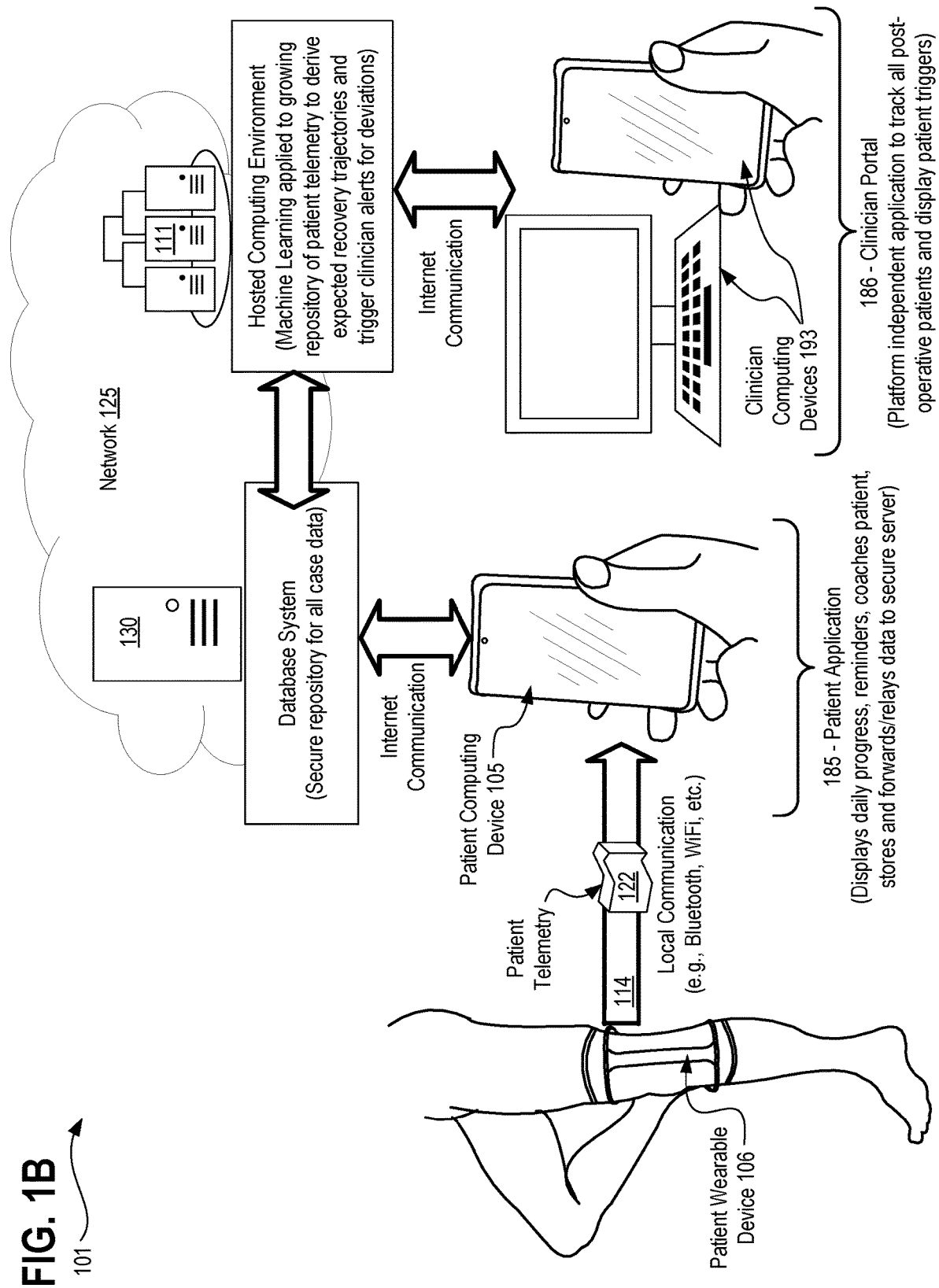
FIG. 1B depicts another exemplary architecture in accordance with described embodiments.

FIG. 1B depicts another exemplary architecture 101 in accordance with described embodiments.

As can be seen here, the database system 130 and the hosted computing environment 111 remain operable within the cloud and communicably interfaced with other devices via network 125. Further depicted are patient computing device 105 in communication with the database system 130 via internet communication. The patient computing device 105 executes patient application 185 which displays daily progress, reminders, coaches the patient, and stores and forwards or relays data back to a secure server, for instance, by transmitting patient telemetry data 122 back to the database 130 within the network 125 or cloud as shown here.

Further depicted is the patient wearable device 106 which transmits patient telemetry data 122 to the patient computing device 105 via a local wireless communication means, such as Bluetooth or WiFi. The patient computing device 105 then responsively transmits the patient telemetry data 122 to the database system 130 via an Internet connection through network 125.

Clinician portal 186 is introduced here providing a platform-independent application by which to track all post-operative patients and to display patient triggers to the clinician. The clinician portal 186 executes upon clinician computing devices 193 which are communicably interfaced back to the hosted computing environment 111 via an internet connection through network 125. As shown here, the hosted computing environment applies data analysis via machine learning to the growing repository of patient telemetry data to derive expected recovery trajectories and to trigger clinician alerts for deviations.

Apparatuses and methods for body joint rehabilitation systems, devices, and methods are disclosed. Generally, in the figures, elements that may be included in a given example are illustrated. However, elements that are illustrated are not essential to all examples of the present disclosure, and an illustrated element may be omitted from a particular example without departing from the scope of the present disclosure.

According to described embodiments, each patient wearable device 106 is operable in conjunction with a body joint rehabilitation system, which according to certain embodiments, includes a wearable joint rehabilitation device, such as the patient wearable device 106 depicted here, which includes integrated sensors to provide positional data relative to a body joint of a patient over a local communication link 114 to a local patient computing device 105. The local communication link 114 may be wired or wireless and, in wireless embodiments may include a wireless transceiver integrated within the patient wearable device 106 and may employ a local wireless communication standard such as Bluetooth, WiFi, or low energy (LE) Bluetooth.

According to certain embodiments, the positional data forms a portion of the patient telemetry data 122 and includes an indication of static position or a degree of rotation, or range or degree of movement, which may be utilized to derive or determine a range or degree of joint motion. For example, such patient telemetry data 122 may indicate dynamic motion and/or rotation associated with active movement of a particular body joint being monitored by the patient wearable device 106.

According to certain embodiments, positional data within the patient telemetry data 122 may further include basic or raw sensor data, and/or a correlation of such sensor data with one or more types of motion, position, or rotation of the joint (e.g., one or more specific exercises or activities).

The patient computing device 105 depicted here may include a smart mobile telephone, such as an Android platform and protocol compliant smartphone or an iPhone platform and protocol compliant smartphone, upon which an end-user downloads the patient application for execution on the smartphone from a marketplace, such as the Android or iPhone app store marketplaces. Alternatively, the patient computing device 105 may be a local computer or a wireless gateway utilized to execute the patient application 185. In alternative embodiments, the patient is provided with a dedicated device for communication with the patient wearable device which is further capable of executing the patient application 185.

As alluded to above, the patient computing device 105 transmits the positional data of the body joint as captured by the sensors of the wearable patient device 105 over a network 125 to the database system 130 and hosted computing environment 111. Should there be no locally available patient computing device 105 available to relay the patient telemetry data 122 to the database system, then the telemetry data 122 can be downloaded or transmitted to the database system 130 when the patient visits their doctor and brings the patient wearable device with them, in which case, the clinician computing device 193 can be utilized to relay the telemetry data 122 to the hosted computing environment 111 in place of the patient computing device. As noted previously, alternative embodiments contemplate the integration of a wireless communications integrated circuit to transmit telemetry data 122 from the patient wearable device 106 to the database system 130 over network 125 utilizing digital or analog cellular communication technologies such as LTE, 3G, 4G, 5G, etc., thus bypassing the local patient computing device 105 entirely.

FIG. 2A depicts multiple views of a wearable harness 200 embodying the wearable patient device in accordance with described embodiments.

As shown here, there is a wearable joint rehabilitation device or wearable harness 200 in accordance with the described embodiments. The wearable harness may be worn about a patient's body joint, such as a knee body joint 250 as depicted here, or shoulder, or elbow, or hip, etc. Notably, the wearable harness does not occlude, cover, or otherwise interfere with the surgical site 251 depicted here as a series of stitches for an incision on the patient's knee.

According to the various embodiments, the wearable harness 200 or wearable joint rehabilitation device includes at least a first attachment, depicted here as the top fastener 265 or a top "smart buckle" as well as a second attachment, depicted here as the bottom fastener 254, also a smart buckle. The top fastener 265 is affixed to a proximal strap 256 that is to be positioned upon a patient's body above a joint as depicted on the left with the patient's leg in a vertical position. The bottom fastener 254 is affixed to a distal strap which is to be positioned upon the patient's body below the joint, again, when oriented in relation to a vertically positioned leg, as shown here.

There is further depicted a connecting section 260 which extends between and couples attachments the proximal and distal straps 256 and 254 respectively, so as to provide both a structural connection between the proximal and distal straps 256 and 254 as well as to provide wired connectivity between the top and bottom fasteners in accordance with certain embodiments.

According to certain embodiments, the wearable harness or wearable patient device 200 may include only one connecting section 260 which may extend along and be connected with any portion of the proximal and distal straps 256 and 254 whereas in other embodiments, two connecting sections 260 are provided. However, a single connecting section 260 is depicted here as a preferred embodiment as it simplifies the process of attaching the wearable harness to a post-operative patient's joint by strapping the wearable harness around the patient's joint rather than necessitating the patient to slip their leg or arm through the wearable harness. While it may seem trivial to have a patient slip their arm or leg through the wearable harness 200, the reality is that such patients, when in a post-operative state, may experience great difficulty and severe pain should they be required to slip their arm or leg through the device in the event of two connecting sections 260, whereas the wearable harness 200 as depicted here with a single connecting section permits the wearable harness to be strapped around the patient's leg or arm or another joint without necessitating any movement by the patient, thus potentially reducing difficulty and pain on behalf of the patient.

According to an alternative embodiment of the wearable harness 200, the wearable harness 200 is worn as a joint rehabilitation device with the single connecting section 260 extending along only one quadrant of a periphery of body portions of the patient, such that the single connecting section 260 connects to about 25% or less of each of the proximal and distal straps 256 and 254. In other embodiments, the wearable harness 200 may be utilized as a wearable joint rehabilitation device insomuch that it is worn with the single connecting section 260 extending along a medial or a lateral side of a patient's leg or arm. In yet other embodiments, the wearable harness 200 may be utilized as a wearable joint rehabilitation device may be worn such that the single connecting section 260 extends along a ventral or a dorsal side of a patient's appendage, whereas in alternative embodiments with two connecting sections between the proximal and distal straps 256 and 254, a first and second connecting section may extend along both medial and lateral sides of the patient's body joint, or along both ventral and dorsal sides of the patient's body joint, or along any combination or all of medial, lateral, dorsal, and ventral sides of the patient's body joint.

Figure 2B:
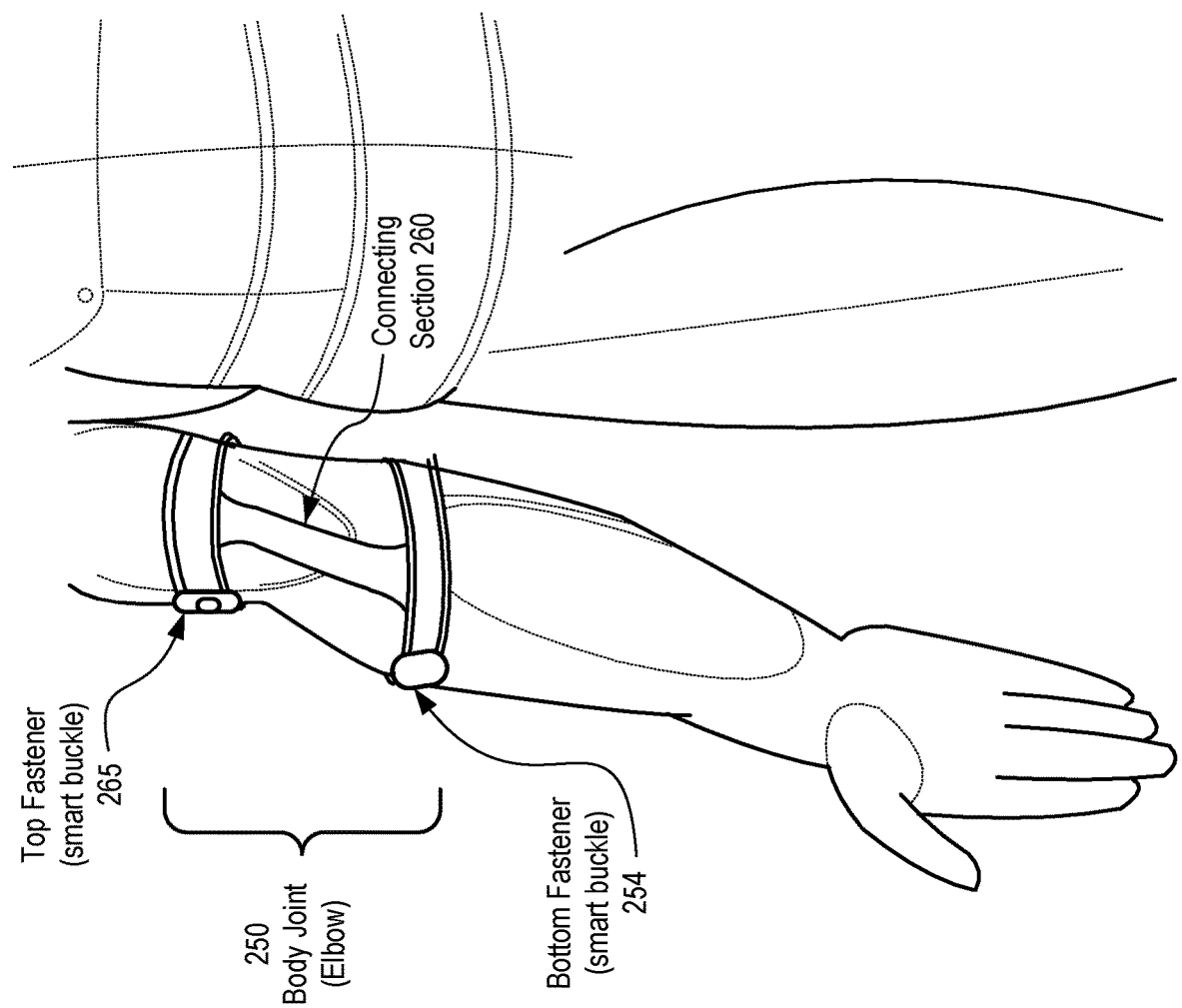
FIG. 2B depicts an alternative view of a wearable harness embodying the wearable patient device in accordance with described embodiments.

FIG. 2B depicts an alternative view of a wearable harness 201 embodying the wearable patient device in accordance with described embodiments.

Whereas the prior figure depicted the wearable harness 201 worn around a knee, here the body joint 250 depicted upon the patient's body is an elbow, again having the wearable harness 201 worn in such a way that a top fastener 265 is attached to a proximal strap which is positioned above the elbow body joint 250 as shown here in this vertical orientation, and there is further a bottom fastener 254 which is affixed to a distal straps which is positioned below the elbow body joint 250 when depicted in this vertical position. The connecting section 260 is again shown as connecting the proximal and distal straps and according to certain embodiments, further providing a path for wired connectivity between the sensors and integrated circuits within the top and bottom smart buckles.

Figure 3:
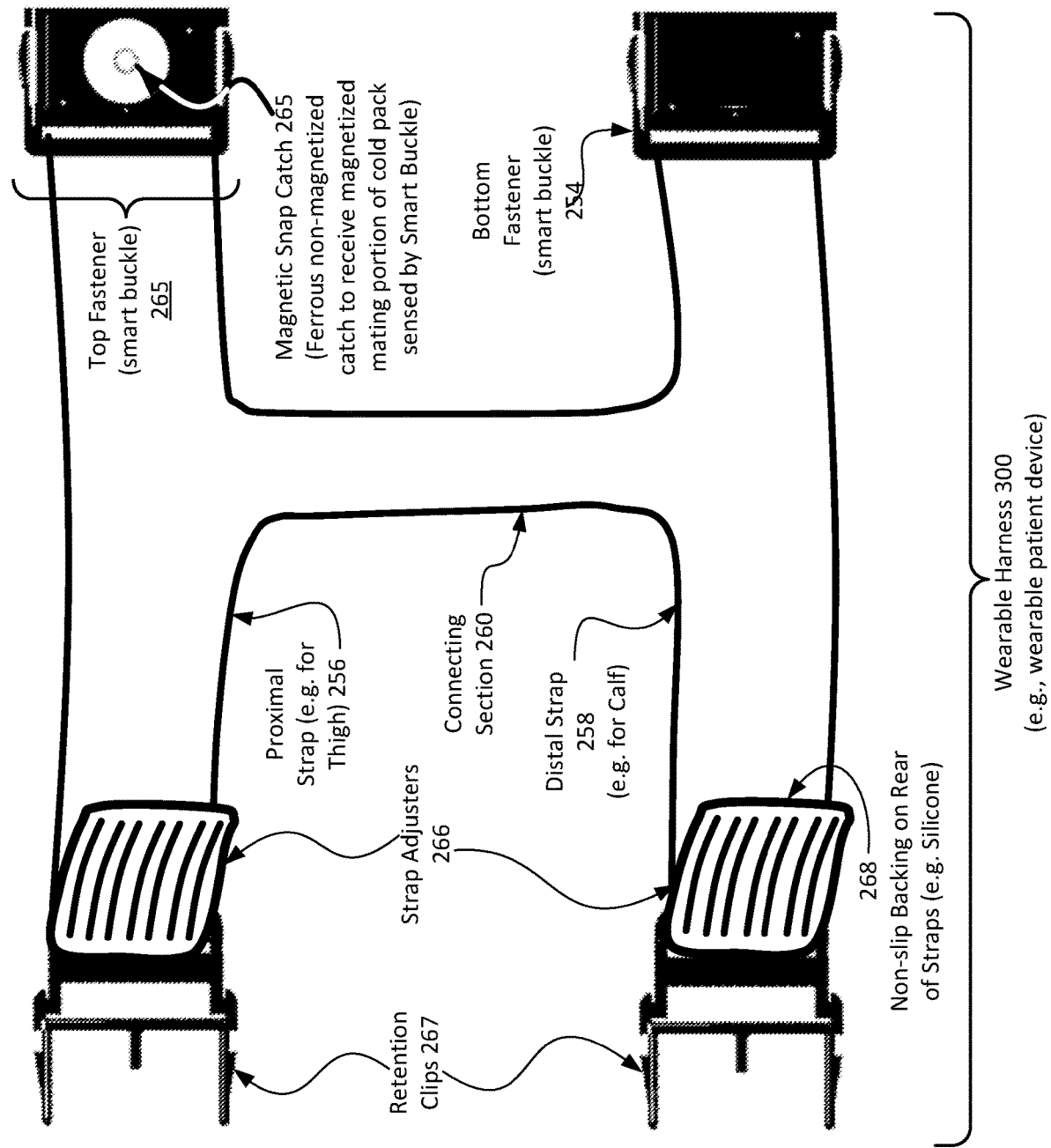
FIG. 3 depicts a front view of a wearable harness embodying the wearable patient device in accordance with described embodiments.

FIG. 3 depicts a front view of a wearable harness 300 embodying the wearable patient device in accordance with described embodiments.

Depicted here is the proximal strap 256, for instance, to be strapped around a patient's thigh assuming treatment of a knee body joint. There is further depicted the distal strap 258, for instance, to be strapped around a patient's calf, again assuming treatment of a knee body joint.

As shown here, the top fastener 265 and the bottom fastener 254 are both opened, thus exposing the retention clip 267 on the opposing end of each of the proximal and distal straps 256 and 254. The connecting section 260 is depicted between the proximal and distal straps 256 and 254 forming a unified structure and forming the wearable harness 300.

Further depicted here are strap adjusters as well as a non-slip backing on the rear of the straps 268, for instance, formed from silicone or other non-slip material suitable for wearable devices. Additionally depicted is a magnetic snap catch 265 which is formed from a ferrous non-magnetized catch and is configured to receive a magnetized mating portion of a cold pack such that the magnetic interference of the magnetized portion may then be sensed by the smart buckle to determine that an ice pack has been affixed to the wearable harness 300.

Figure 4:
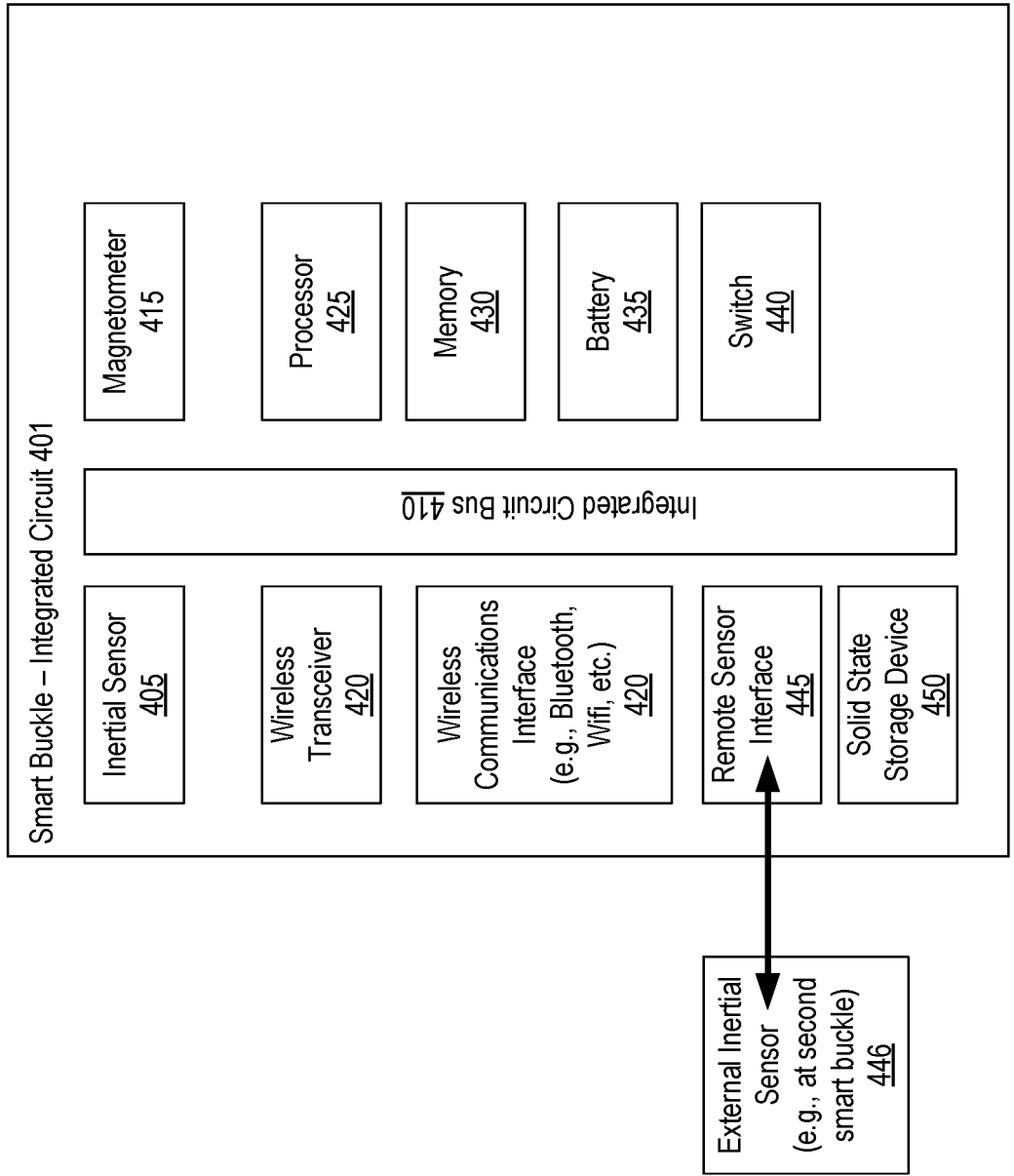
FIG. 4 depicts a block diagram of components integrated within an exemplary smart buckle's integrated circuit, in accordance with described embodiments.

FIG. 4 depicts a block diagram of components integrated within an exemplary smart buckle's integrated circuit, in accordance with described embodiments.

As described before, there is circuitry embedded within the smart buckle which is attached to the wearable harness for use as a wearable joint rehabilitation device. As shown here, such a smart buckle includes an integrated circuit bus 410 to provide intercommunications amongst the various components, with such components including an inertial sensor 405, a magnetometer 415, a processor 425, memory 430, a battery 435, a switch 440, a wireless transceiver 420, a remote sensor interface 445 communicably linked with an external inertial sensor 446, for instance, such as a second sensor at the second smart buckle, and a solid-state storage device 450 for telemetry and other data storage.

A single wearable harness may include two identical smart buckles which communicate with one another and provide redundancy or may utilize a single smart buckle with the described components and then further include a second smart buckle which is less costly and provides fewer components. For instance, such a second smart buckle may include only the second inertial sensor which is external to the first smart buckle and communicates with and reports to the first smart buckle, or may include an additional battery, or may include a subset, but not all, of the components depicted with respect to the smart buckle integrated circuit 401 as shown here. According to such embodiments, the two smart buckles may communicate via a wired communications path which is routed through the connecting section of the wearable harness.

The first inertial sensor 405 may be an accelerometer and/or a gyroscopic sensor. Similarly, the second inertial sensor shown here as the external inertial sensor 446 may also be an accelerometer and/or a gyroscopic sensor, each being integrated into the respective first and second smart buckles that are in turn fixedly attached to the proximal and distal straps 256 and 254 of the wearable harness.

The first and second inertial sensors 405 and 446 provide respective first and second inertial sensor data. The processor 425 operates in communication with the first and second inertial sensors 405 and 446 and receives receive the first and second inertial sensor data to provide positional data about the body joint.

As depicted here, the processor 425 is integrated within the first smart buckle, however, may be integrated within either or both smart buckles affixed to the wearable harness and operate in conjunction with the first and second inertial sensors 405 and 446 to execute stored processing instructions and process incoming positional data. The wireless transceiver 420 provides communication over a local communication link, such as Bluetooth or WiFi.

Battery 435 operates in conjunction with one or more activation and/or power switches to activate circuit components of the smart buckle integrated circuit 401, including inertial sensors 405 and 446, processor 425, and the other processing components.

In some embodiments, circuit components of the wearable harness for use as a wearable joint rehabilitation device, including the circuit components and inertial sensors shown here is configured with sufficient battery life and/or energy storage capacity to operate the smart buckle integrated circuit 401 throughout the entire prescribed rehabilitation regimen. As a result, a patient does not need to replace or recharge the battery during his or her rehabilitation. Configuring the circuit components and inertial sensors to operate in such a manner may increase the convenience of a patient using a wearable joint rehabilitation device and thus in turn improve compliance with the prescribed rehabilitation regimen.

According to certain embodiments, different sized battery 435 components are configured for different models of the smart buckle integrated circuit 401 such that longer prescribed rehabilitation regimens may be accommodated through the selection of a longer life smart buckle integrated circuit, thus negating the need for the patient to have to recharge or replace the battery during their rehabilitation phase, despite being prescribed a longer rehabilitation regimen.

Figure 5A:
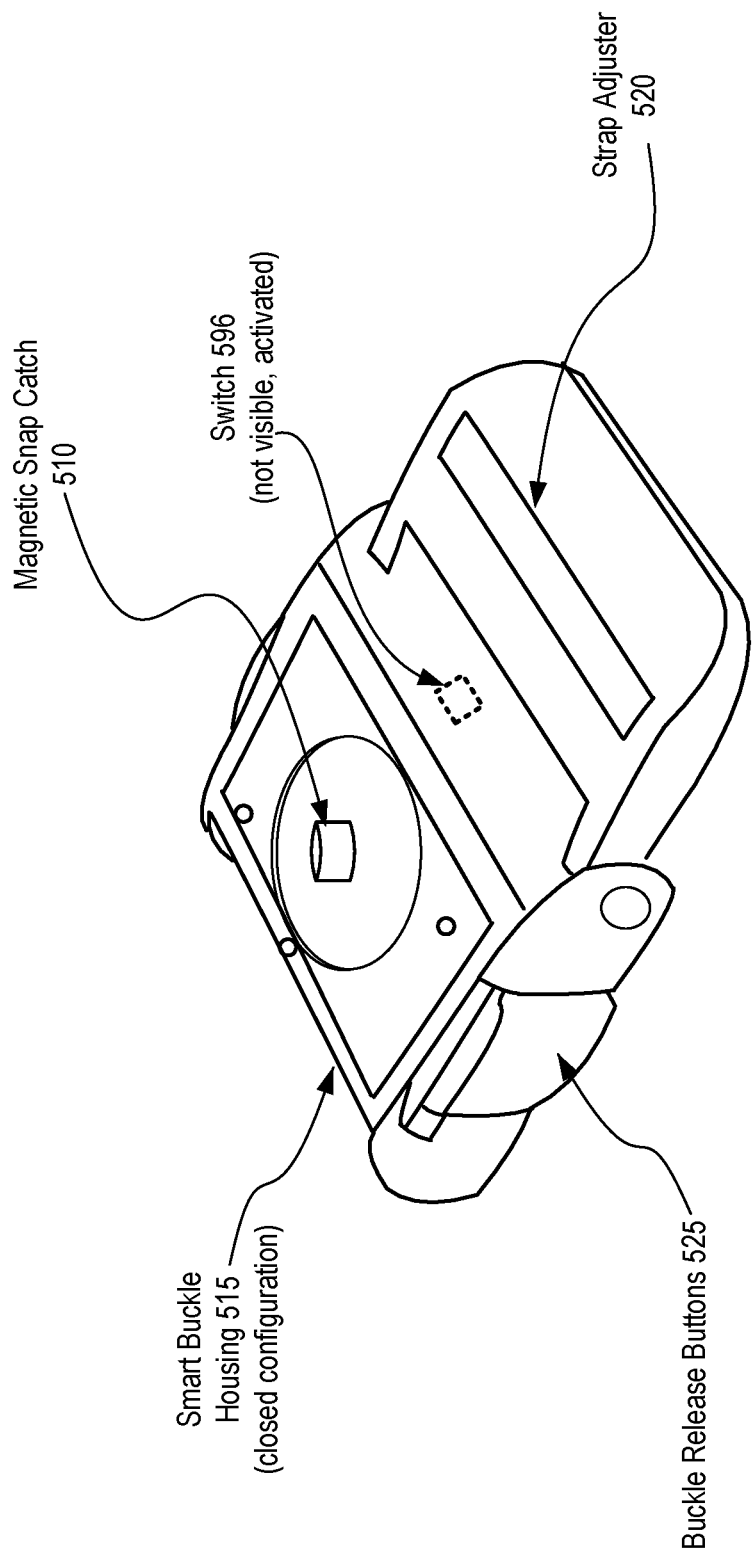
FIGS. 5A and 5B depict an exemplary smart buckle diagram in its closed (FIG. 5A) and open (FIG. 5B) configurations, within which the smart buckle circuit components are integrated, in accordance with described embodiments.
Figure 5B:
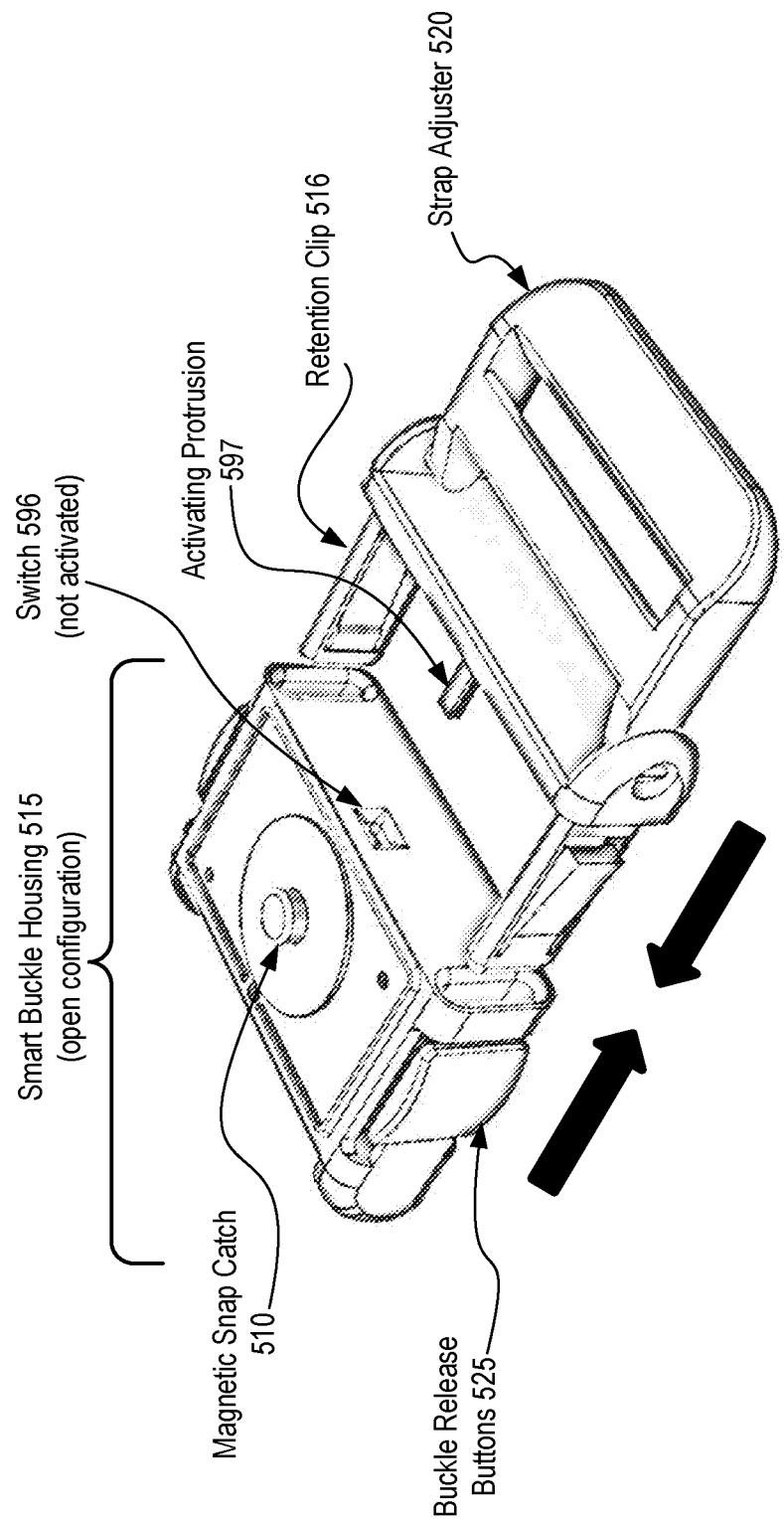

FIGS. 5A and 5B depict an exemplary smart buckle diagram in its closed (FIG. 5A) and open (FIG. 5B) configurations, within which the smart buckle circuit components are integrated, in accordance with described embodiments.

In particular, there is depicted here, a smart buckle housing 515 in both the open position at the top of the figure as well as the smart buckle housing 515 in its closed position at the bottom of the figure. Further depicted are the strap adjusters 520, and the buckle release buttons 525.

Notably, there is depicted the magnetic snap catch which is itself non-magnetized but formed from a ferrous material such that it will receive and magnetically hold a magnetic snap. In such a way, the magnetometer of the smart buckle integrated circuit is enabled to sense the presence or lack thereof, of the ice pack due to the electromagnetic interference when of the magnetic snap affixed to such an ice pack when brought into close proximity and attached to the magnetic snap catch of the smart buckle housing.

As depicted here, the smart buckle includes first and second complementary mating body members that may releasably snap/lock together to form the open and closed positions respectively. The retention clip 516 portion includes tabs to engage complementary catches formed within the smart housing 515 portion of the smart buckle. In addition, the retention clip portion may include one or more additional tabs or protrusions 597 to activate a switch 596 mounted on the smart buckle housing 515 portion or to activate the circuitry components of the smart buckle housing.

For example, the switch may be utilized to detect closure of the smart buckle housing 515 with the retention clip, which then in turn energizes the smart buckle and prepares the wearable harness for use by a patient, by transitioning the device from a low energy consumption sleep state and into a normal operational state. In certain embodiments, times during which switch is activated may be measured or determined to provide an indication of durations and/or times during which smart buckle is closed, thus providing a record or patent telemetry data indicating when and/or how often or how long the wearable harness is worn and used as a joint rehabilitation device by a patient. As described above, the smart buckle housing 515 embeds within it the smart buckle circuit components. In some embodiments, smart buckle circuit components may be removably mounted in or on the smart buckle so that circuit components may be removed from the smart buckle for repair, re-use, and/or recycling. For instance, in certain embodiments, the battery is re-charged before use by another patient, whereas in other embodiments, the battery is replaced.

Figure 6:
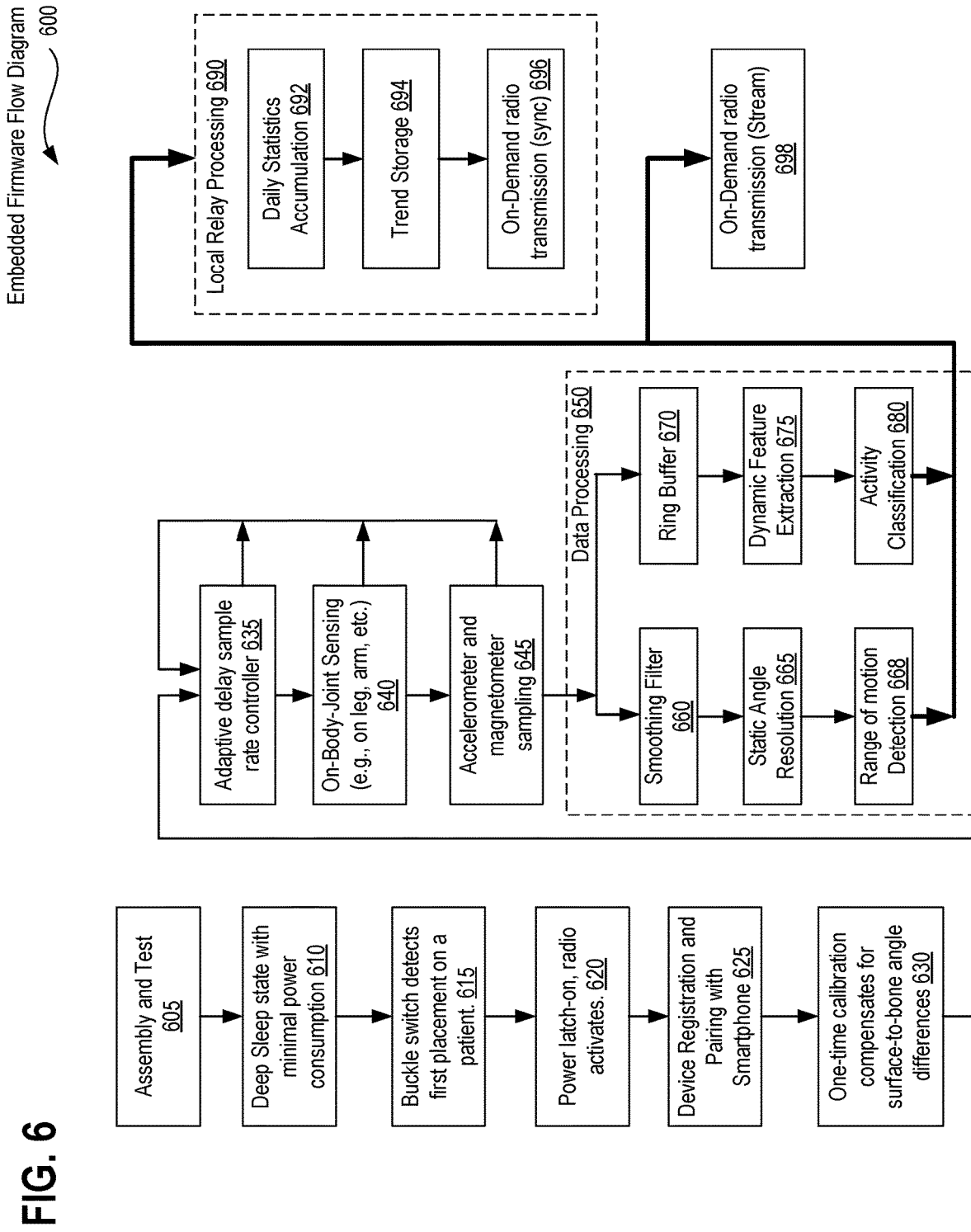
FIG. 6 depicts a flow diagram illustrating a method for integrating a body joint rehabilitation regimen with a wearable movement capture device which is operable in conjunction with a cloud based computing environment in accordance with described embodiments.

FIG. 6 depicts a flow diagram illustrating a method 600 for integrating a body joint rehabilitation regimen with a wearable movement capture device which is operable in conjunction with a cloud based computing environment. As depicted here, the flow diagram illustrates the embedded firmware of a wearable harness, which may be prescribed to a patient for use as a wearable joint rehabilitation device in accordance with described embodiments.

Method 600 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the hosted computing environment 111, the web-services bridge 190, and its database system 130 as depicted at FIG. 1, and other systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

Beginning with operation 605, method 600 includes initial assembly and test of a wearable joint rehabilitation device. In embodiments, initial assembly and test of a wearable joint rehabilitation device may include providing battery power to the circuitry and initial performance testing of a wearable joint rehabilitation device in association with manufacture or refurbishment of the wearable joint rehabilitation device.

At operation 610, method 600 includes setting circuitry of a wearable joint rehabilitation device into a "deep sleep" state. In some embodiments, the deep sleep state may draw negligible or no power from a battery included in the wearable joint rehabilitation device, which may therefore be suitable for shipment and/or storage until activation for use.

At operation 615, method 600 includes detecting activation of the wearable joint rehabilitation device for usage. Activation of the wearable joint rehabilitation device for usage may include detection of applying the wearable joint rehabilitation device to a patient. In some embodiments, activation of the wearable joint rehabilitation device for usage may include engagement of a buckle to attach the wearable joint rehabilitation device to a patient.

At operation 620, method 600 includes activation of circuit components of the wearable joint rehabilitation device, which may include activation of a wireless communication link of the wearable joint rehabilitation device. For instance, the latch closure may trigger a power latch-on radio event to activate the radio transceiver of the smart buckle integrated within the wearable harness forming the wearable joint rehabilitation device.

At operation 625, method 600 includes registration and pairing of the wearable joint rehabilitation device with a local computing device. In some embodiments, the local computing device may include a computer and/or a smart mobile telephone local to the wearable joint rehabilitation device.

At operation 630, method 600 includes a calibration of the wearable joint rehabilitation device with respect to the patient. In some embodiments, for example, the calibration may include determination of wearable joint rehabilitation device orientations and/or positions with regard to pre-defined patient joint positions. For example, a patient may be instructed by a healthcare provider to position the joint in selected positions or orientations in standing, seated, or supine positions.

At operation 635, method 600 includes application of an adaptive delay sample rate control to acquisition of data from the wearable joint rehabilitation device. For example, based on relative orientations detected by the wearable joint rehabilitation device and/or prolonged absence of motion that may correspond to the wearable joint rehabilitation device having been removed from and/or not being worn by the patient, the adaptive delay sample rate may be set to a low-rate resting mode, with a prolonged period (e.g., 3 to 5 seconds) between sample acquisitions. Such a resting mode may provide decreased power usage, with increased battery operating life, while also providing automatic re-activation upon subsequent detection of motion and/or position or orientation.

At operation 640, method 600 includes a determination or indication that the wearable joint rehabilitation device is sensed via an on-body-joint event to detect that the wearable harness has been placed upon a patient's joint undergoing rehabilitation. In some embodiments, sensing that the wearable joint rehabilitation device is on a body joint undergoing rehabilitation includes detection of motion and/or a position or orientation corresponding to the wearable joint rehabilitation device being worn on a body joint undergoing rehabilitation.

At operation 645, method 600 includes sampling of motion and/or position or orientation data by the wearable joint rehabilitation device. In some embodiments, sampling of motion and/or position or orientation data by the wearable joint rehabilitation device may include sampling of inertial data and/or magnetometer data provided by circuit components of the wearable joint rehabilitation device. Such motion and/or position or orientation data may be referred to herein as spatial rehabilitation data.

At block 650, on-device data processing is applied, including processing of spatial rehabilitation data to provide positional data about the body joint. On-device data processing 650 may be implemented according to a wide range of embodiments, and the depicted on-device data processing operations 650 corresponds to one example implementation.

Operation 660 indicates that a smoothing filter may be applied to the spatial rehabilitation data, which may smooth the data and decrease or eliminate excessive and/or extraneous variations in the data.

Operation 665 indicates that a static angle resolution may be determined from the spatial rehabilitation data. The static angle resolution may correspond to the joint angle as measured with a conventional mechanical goniometer and may provide a range-of-motion detection 668 by recording the maximum and minimum joint angles reached within a period of time.

Operation 670 indicates that the spatial rehabilitation data is buffered in a sequential queue. In some embodiments, the buffering may include operation of a ring buffer.

Operation 675 indicates that buffered spatial rehabilitation data are processed to extract dynamic features (e.g., time-dependent variations in acceleration and rotation). In some embodiments, extracting dynamic features from the buffered spatial rehabilitation data may include correlating said time-dependent variations with predetermined patterns that correspond to selected activities.

Operation 680 indicates that a dynamic feature extracted from the spatial rehabilitation data may be classified as a selected activity. With regard to a knee joint, for example, selected activities according to which a dynamic feature may be classified may include any or all of static knee position and/or bend, active knee bends (e.g., prone, supine, seated, and/or standing), walking, climbing and/or descending stairs, etc.

Operations 690 indicate that positional data of the body joint provided according to operations 650, for example, may be accumulated and stored on the wearable joint rehabilitation device in preparation for intermittent radio transmission (sync) to a local computing device. Operations 690 may be implemented according to a wide range of embodiments, and the following embodiment of operations 690 corresponds to one example implementation.

Operations 692 indicate operations by which one or more batches of positional data may be accumulated before transmitting to the local computing device. Daily statistics accumulation 692, for example, may involve counting steps walked, stairs climbed, time standing, etc. for the present 24-hour period. At midnight, the set of statistics for the day just completed may be moved to permanent trend storage 694. Thus, trend storage has data from every day that the apparatus has been in use, and trends can be ascertained by comparing individual statistics over a period of multiple days or weeks Operation 692 further indicates that positional data may be accumulated by the wearable joint rehabilitation device for a selected time period (e.g., a day), or until positional data are transmitted to a local computing device. In some examples, daily statistics accumulation may include counting steps walked, stairs climbed, time standing, etc. for each 24-hour period.

Operation 694 indicates that trend data may be stored at the wearable joint rehabilitation device with the accumulated positional data. For example, once a day (e.g., at midnight) the daily statistics accumulation for each day from operation 220 may be moved to a portion of the memory on wearable joint rehabilitation device referred to as trend storage. Thus, trend storage may have data from multiple days or every day that the wearable joint rehabilitation device has been in use. The data in the trend storage may allow trends to be ascertained by comparing individual statistics over a period of multiple days or weeks.

Operation 696 indicates that accumulated positional data and trend data may be transmitted to a local computing device in synchronization mode. In some embodiments, such transmissions may be periodic, on a regular schedule, or may be episodic, to provide data synchronization (e.g., at high data speed) such as when the wearable joint rehabilitation device is in communication with the local computing device. In some examples, the data may be transmitted "on-demand," such as in response to a request for the transmission from a local computing device.

Operation 698 indicates that the positional data of the body joint may be transmitted as generated in "streaming" mode. For example, transmitting the positional data as a stream may include a real-time transmission of positional data as it is collected, such as for use in providing real-time feedback to the patient. In some examples, the positional data may be transmitted as a stream and "on-demand," such as in response to a request for the transmission from a local computing device. In some embodiments, the transmission may employ wireless transmission, and transmitting of the positional data of the body joint may occur so long as the wearable joint rehabilitation device is in communication with the local computing device.

According to another embodiment of method 600, there is a method performed by system having at least a processor and a memory therein, in which the method includes performing operations via a wearable joint rehabilitation device, having a first and a second attachment that are attachable to be held at respective first and second body portions with a body joint between them; and first and second inertial sensors coupled with the first and second attachments to be held at the first and second body portions to provide first and second inertial sensor data, respectively; and a processor in communication with the first and second inertial sensors to receive the first and second inertial sensor data to provide positional data of the body joint. Wherein the wearable apparatus is to monitor activity of a body joint such as knee or elbow for rehabilitation and recovery after surgical procedures and after injury.

According to another embodiment, the wearable apparatus further includes a communication link in communication with the processor to communicate the positional data of the body joint to a separate computing device.

According to another embodiment, the wearable apparatus further includes a wireless transceiver to provide a proximal wireless link to a proximal computing device.

According to another embodiment, the wireless transceiver employs Bluetooth standard communication.

According to another embodiment, the first and second attachments include first and second buckles to which are coupled the first and second inertial sensors, respectively, and the processor is coupled to the first buckle with the first inertial sensor.

According to another embodiment, the wearable apparatus further includes a connecting structure coupling the first and second attachments, and an electrical coupling carried by the connecting structure to carry communication between the processor and the second inertial sensor.

According to another embodiment, the wearable apparatus further includes a thermal detector sensor in communication with the processor to provide an indication of application of temperature therapy proximal to the device.

According to another embodiment, the wearable apparatus further includes a temperature therapy appliance coupling to provide a coupling between the device and a temperature therapy appliance.

According to another embodiment, the first attachment includes a magnetic detector to detect a stray magnetic field of the magnetic fastener of the temperature therapy appliance as the indication of application of temperature therapy proximal to the device.

According to another embodiment, the body joint is a hinge body joint.

According to another embodiment, the hinge body joint is a knee.

According to yet another embodiment, there is a wearable joint rehabilitation device to provide positional data of a body joint of a patient over a local communication link to a local computing device; and a network computing system to receive from the local computing device the positional data of the body joint and to provide a correlation of statistics and trends regarding the positional data of the body joint with a basis of joint rehabilitation data.

According to another embodiment, the network computing system is further configured to provide to a healthcare provider access to the statistics and trends regarding the positional data of the body joint and a correlation of said statistics and trends with expected values.

According to another embodiment, the network computing system is a host organization or a cloud based storage repository to provide on-demand services, wherein the network computing system is further configured to provide to a healthcare provider an alert if the statistics and trends regarding the positional data deviate from expected values for a similar population of patients by at least a threshold amount.

According to another embodiment, the local computing device is a patient's computing device and is further configured to provide to the patient information relating to the positional data of the body joint.

According to another embodiment, the information relating to the positional data of the body joint includes any or all of progress in the motion of the body joint, reminders about performing motion of the body joint, and/or coaching about motion of the body joint to be performed.

According to another embodiment, the local communication link includes a local wireless communication link, such as a wireless link to a mobile telephone.

According to another embodiment, the there is a wearable joint rehabilitation device which includes first and second attachments that are attachable to be held at respective first and second body portions with a body joint between them; first and second inertial sensors coupled with the first and second attachments to be held at the first and second body portions to provide first and second inertial sensor data, respectively; and a processor in communication with the first and second inertial sensors to receive the first and second inertial sensor data to provide the positional data of the body joint.

According to another embodiment, there is a wearable device buckle, including: first and second complementary mating body members, in which at least one of the first and second complementary mating body members includes a tab to engage a complementary catch on the other of the first and second complementary mating body members; and an inertial sensor coupled with one of the first and second complementary mating body members to provide inertial sensor data.

According to another embodiment, the wearable apparatus or the wearable device buckle further includes a processor in communication with the inertial sensor to receive the inertial sensor data to provide positional data regarding the buckle.

According to another embodiment, such a device further includes a communication link in communication with the processor to communicate the positional data to a separate computing device.

According to another embodiment, such a device includes a battery and a battery activation switch coupled to the battery to activate the battery upon a coupling of the first and second complementary mating body members.

According to another embodiment, the battery activation switch is configured with associated circuitry to activate the battery fixedly upon an initial coupling of the first and second complementary mating body members.

According to another embodiment, such a device further includes an appliance coupling and a sensor in communication with the processor, in which the attachment sensor is to provide to the processor an attachment indication when an appliance is attached to the appliance coupling; for example, such a sensor includes a magnetometer and the appliance includes a magnet to activate the magnetometer when the appliance is attached.

As described above with respect to FIG. 1A, the database system 130 or the host organization 111 may receive the positional data of the body joint and provide a correlation of the positional data of the body joint with a basis of joint rehabilitation data. In some embodiments, the body joint may be a hinge body joint, such as a knee or elbow. In some embodiments, the basis of joint rehabilitation data may be specifically designed for a single patient or used more generally for a number of patients. In addition, the host organization 110 may provide a healthcare provider access to the daily statistics for motion of the patient's body joint and the correlation of the statistics with expected values of the positional data. In some embodiments, host organization provides an alert to the healthcare provider if the daily statistics, or a trend representing a progression of such statistics over several days or weeks, deviate from the expected course of recovery by at least a threshold amount. For example, such deviations may indicate that a patient is not completing prescribed rehabilitation exercises or that rehabilitation of the joint (e.g., range of motion) has not progressed as expected.

In such a way, the body joint rehabilitation system may be used in rehabilitation of a joint following an injury or a medical procedure (e.g., surgery) to correct or treat an injury. In connection with rehabilitation of a joint following a medical procedure (e.g., post-procedure or post-op rehabilitation), for example, the basis of joint rehabilitation data may encompass data for a statistically large number patients from which a provider may discern a standard or expected rehabilitative progression over time. Positional data, including daily statistics and/or accumulated positional data from a patient may allow a provider to determine if the patient's rehabilitative progress fits within an expected rehabilitative progression and, if not, determine whether prescribed rehabilitative exercises are being performed or if rehabilitation is being slowed by other health factors, which may include slow healing, infection, re-injury, etc.

Similarly, the patient computing device (at elements 105A-C of FIG. 1A), local to the patient wearable device, may provide to the patient information relating to the positional data of the body joint. The information relating to the positional data of the body joint may include any or all of progress in the motion of the body joint, reminders about performing motion of the body joint, and/or coaching about motion of the body joint to be performed. The information may be generated by the patient computing device based on the positional data of the body joint, or may be received by the patient computing device from the host organization 110.

Figure 7A:
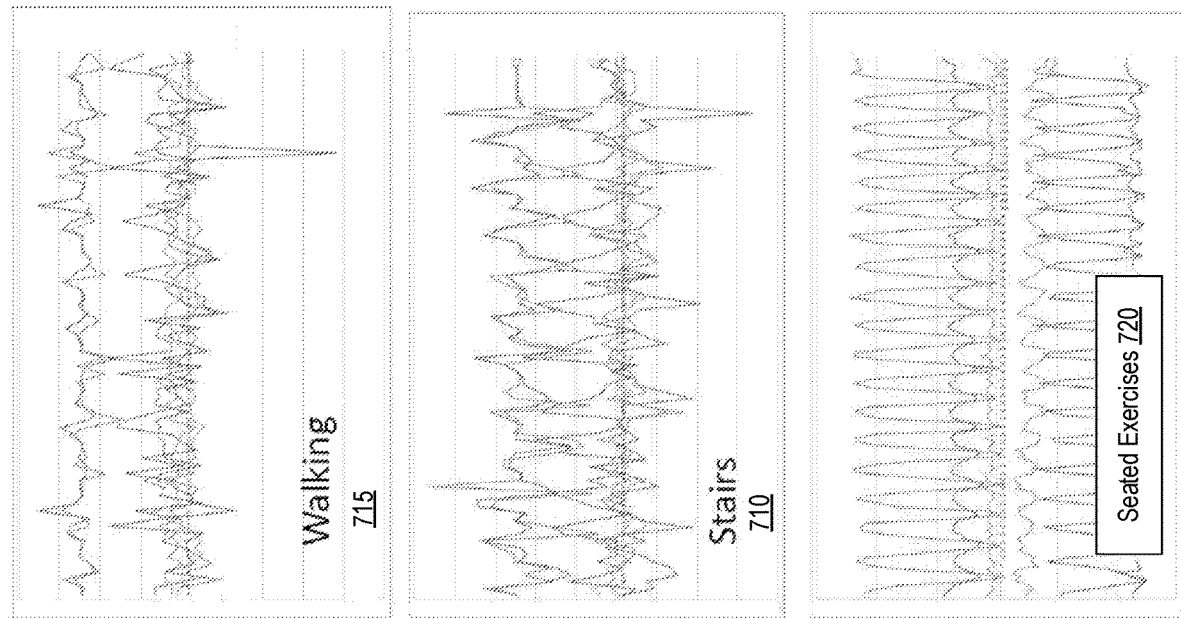
FIG. 7A depicts example graphs illustrating basic sensor data from which static and/or dynamic motion may be determined for, respectively, flat walking, stepping on stairs, and seated exercise in accordance with described embodiments.
Figure 7A:
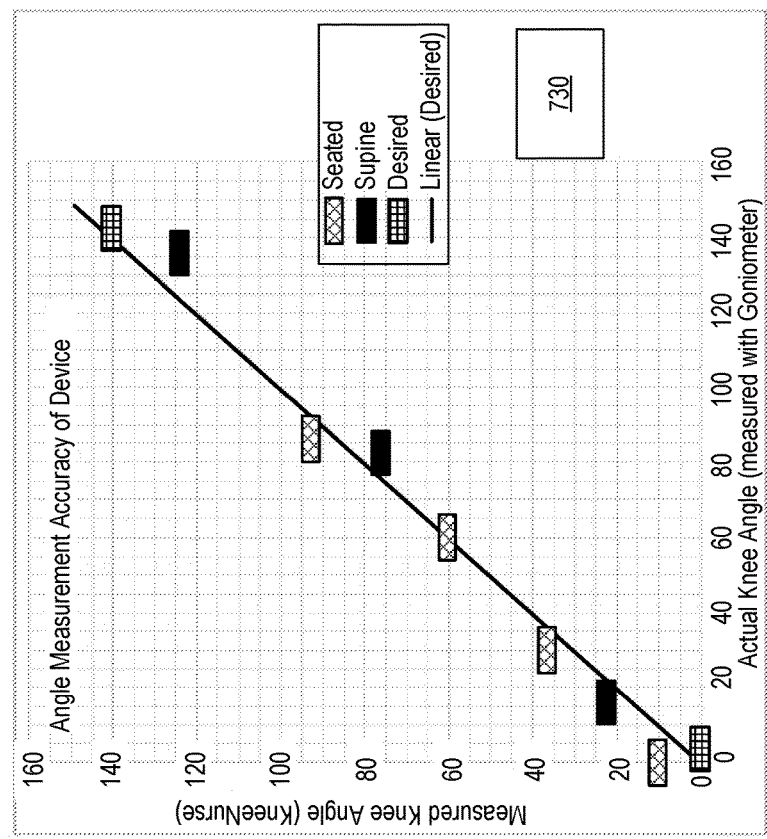

FIG. 7A depicts example graphs 710, 715, 720, and 730 illustrating basic sensor data from which static and/or dynamic motion may be determined for, respectively, flat walking, stepping on stairs, and seated exercise. Graph 730 illustrates sample angle measurement accuracy of an embodiment of wearable joint rehabilitation device relative to conventional joint angle measurement, such as by goniometer.

Figure 7B:
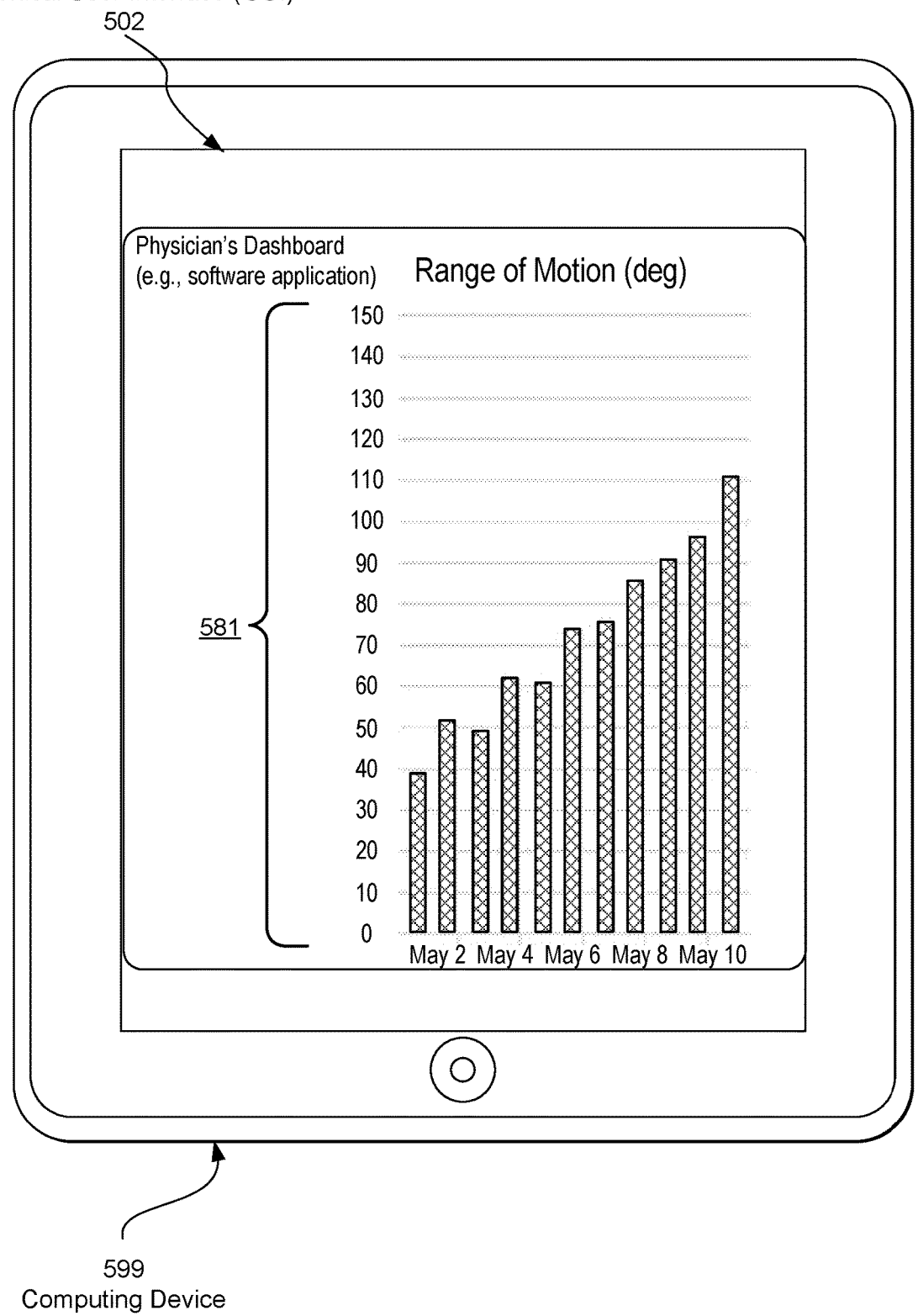
FIG. 7B depicts a Graphical User Interface (GUI) displayed upon a computing device, in accordance with described embodiments.

FIG. 7B depicts a Graphical User Interface (GUI) 502 displayed upon a computing device, in accordance with described embodiments. As depicted here, there is a clinician's computing device displaying a range of motion graph 581 for a particular patient, in which the range of motion is indicated to be improving over time.

Figure 7C:
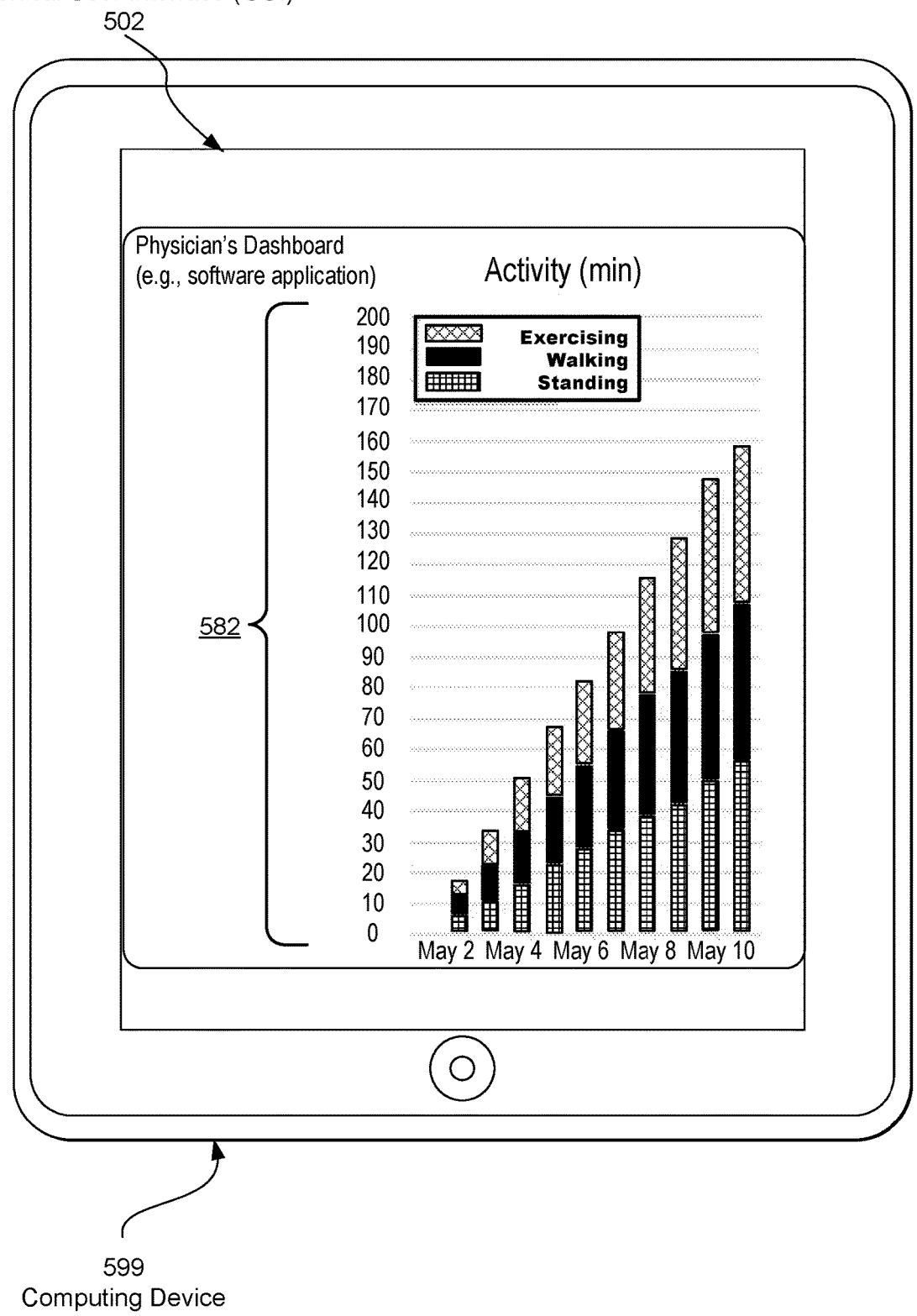
FIG. 7C depicts a Graphical User Interface (GUI) displayed upon a computing device, in accordance with described embodiments.

FIG. 7C depicts a Graphical User Interface (GUI) 502 displayed upon a computing device, in accordance with described embodiments. As depicted here, there is a clinician's computing device displaying an activity graph 582 for a particular patient, in which the daily activity for this patient is indicated to be improving over time.

Figure 7D:
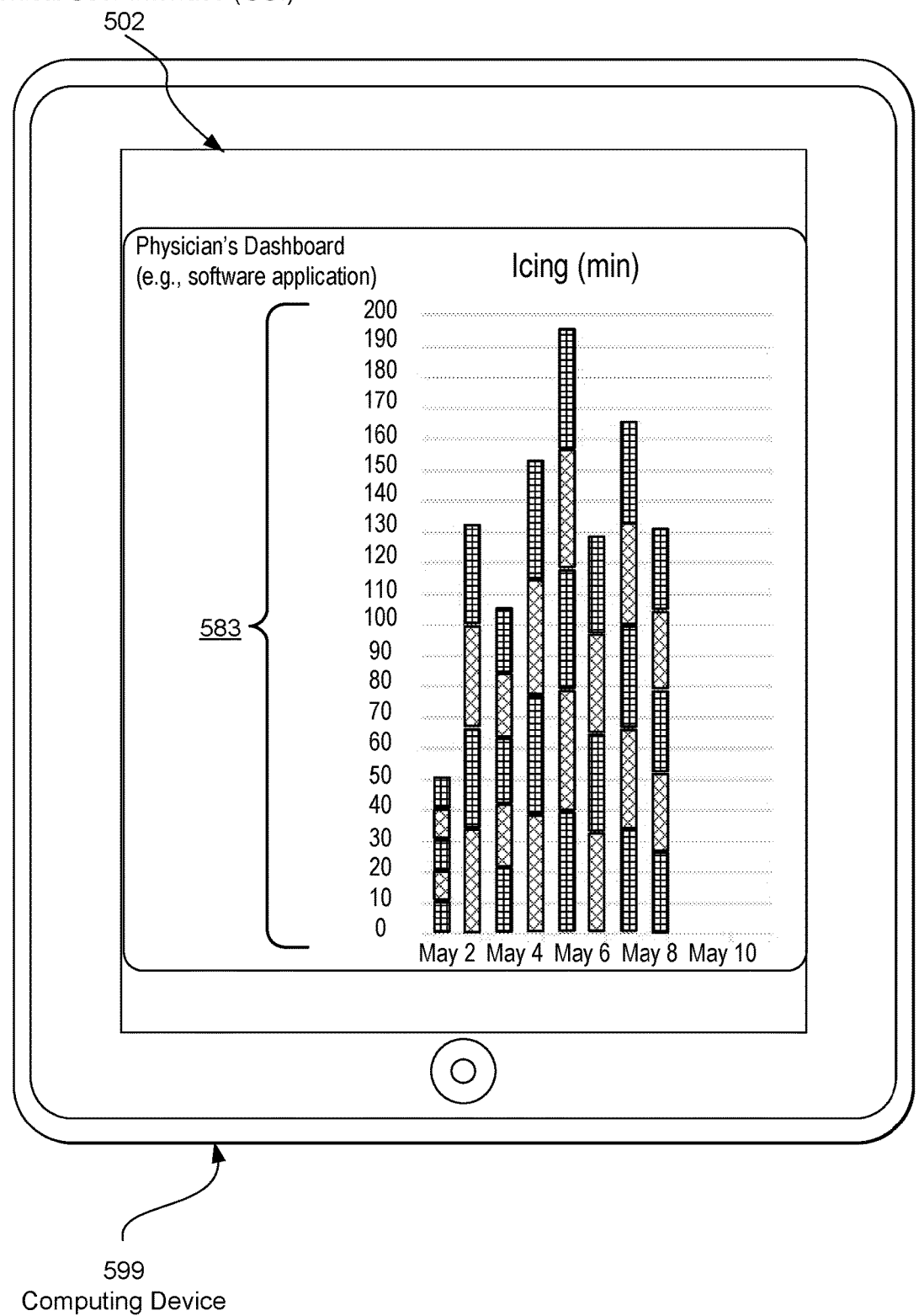
FIG. 7D depicts a Graphical User Interface (GUI) displayed upon a computing device, in accordance with described embodiments.

FIG. 7D depicts a Graphical User Interface (GUI) 502 displayed upon a computing device, in accordance with described embodiments. As depicted here, there is a clinician's computing device displaying an icing application duration graph 583 for a particular patient, in which the daily icing duration for this patient is indicated to be varying over time.

The various graphs depict, for example the actual knee angle at graph 730, and similar data may be provided for other body joints, such as an actual angle of an elbow undergoing rehabilitation. Similarly, the sensor data may collect information from which various activities may be classified and derived. For example, the graph 715 depicts that walking has been detected by the wearable harness. Similarly, the graph at 710 depicts that stairs have been climbed according to detection and classification by the wearable harness. Lastly, graph 720 depicts data indicating that seated exercises were performed.

As shown at element 251 of FIG. 2A, the wearable harness for use as a wearable joint rehabilitation device may include an open region between the proximal and distal straps which allows access to a portion of the patient's body joint, including, for example, one or more incisions that may need dressing changes or other treatments. In addition, the open region may facilitate application of temperature therapy (e.g., cryotherapy or "icing") to joint 50. Cryotherapy (cold therapy) is a traditional mainstay of treatment to reduce swelling, inflammation, and pain. Patient compliance with cryotherapy is often incomplete or absent. Embodiments of wearable harness for use as a wearable joint rehabilitation device and rehabilitation system therefore provide correct sizing and capacity of cold therapy pads or "appliances" for the joint in accordance with certain embodiments, and may therefore encourage timely and consistent temperature treatment applications by electronically monitoring its use. In some embodiments, the rehabilitation system, via the patient's local computing device (e.g., see element 105A-C of FIG. 1A), may provide coaching, encouragements, or a suggestions, to a patient to exercise immediately following cryotherapy, which may takes advantage of the temporary pain relief of cryotherapy to increase range of motion and strength. In some instances, temperature therapy may include application of heat or warmth to a joint or region.

Figure 8:
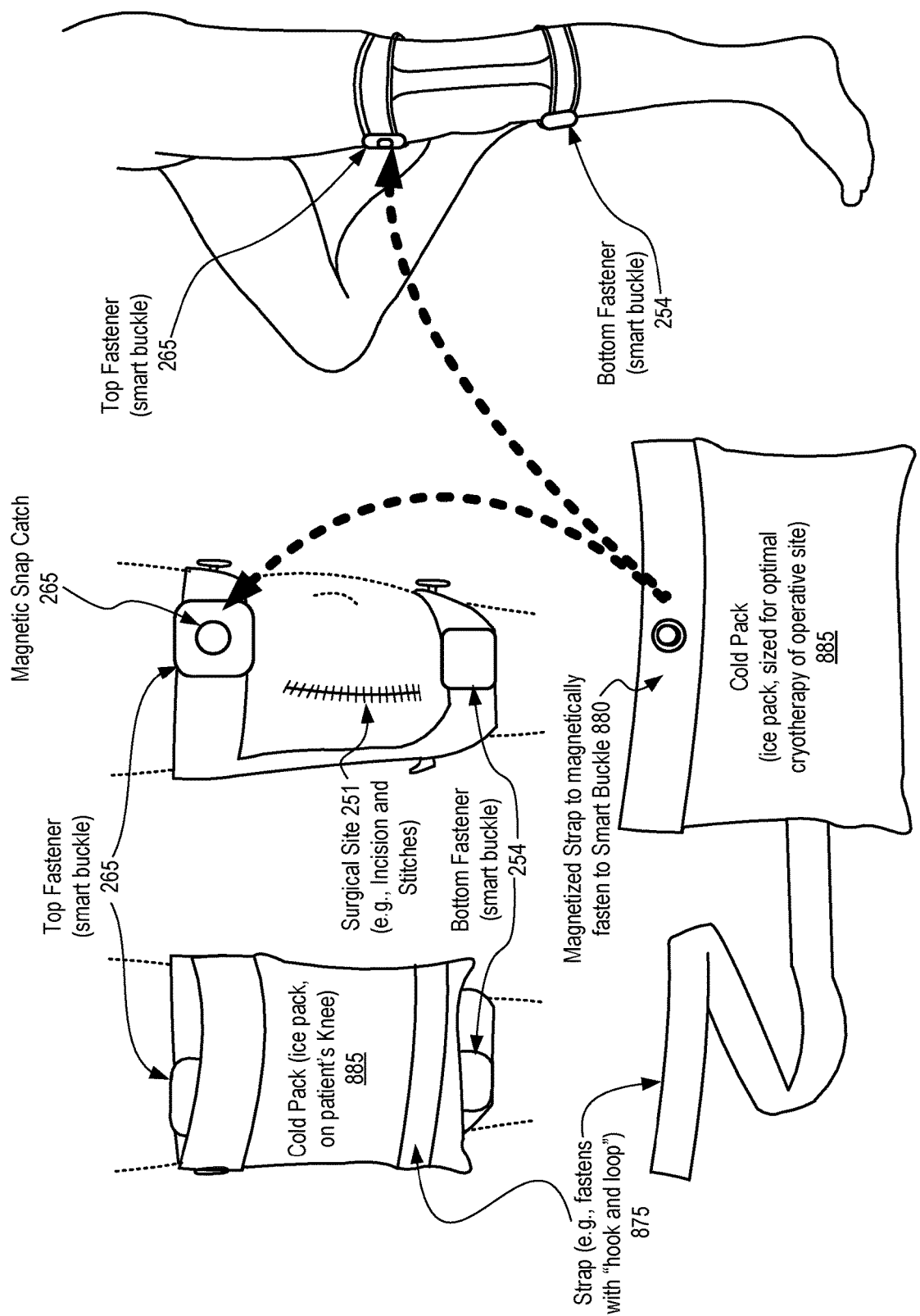
FIG. 8 depicts an exemplary wearable harness for use as a wearable joint rehabilitation device which is to be worn about a patient's body joint with a temperature therapy appliance, such as cold pack or a hot pack, in accordance with described embodiments.

FIG. 8 depicts an exemplary wearable harness for use as a wearable joint rehabilitation device which is to be worn about a patient's body joint with a temperature therapy appliance, such as cold pack 885 or a hot pack, in accordance with described embodiments.

As depicted here, the top fastener smart buckle 265 or the bottom fastener smart buckle 254, or both, include an appliance coupling component, such as the magnetic snap catch 265 shown here. More particularly the magnetic snap catch is non-magnetic but formed from a ferrous material and therefore will receive and magnetically couple with a magnetized ferrous stud affixed to the cold pack 885 or hot pack. For instance, a magnetic snap affixed to the cold pack or hot pack will snap into the top or bottom smart buckle, or both, at the magnetic snap catch, and be retained magnetically. Moreover, the magnetometer internal to the smart buckle will sense the presence of the magnetized ferrous stud, and thus trigger an event indicating to embedded firmware of the wearable harness that an ice pack or heat pack has been attached and is being worn by the patient.

As shown here, the magnetic snap 265 may cooperate with the appliance coupling component (e.g., the magnetized stud and magnetized strap 880) to hold the temperature therapy appliance (e.g., the cold pack 885 or hot pack) in place over a joint, such as the patient's knee, elbow, etc.

Optionally, the magnetized stud and the magnetic snap catch 265 are operable together with a closable strap 875, for instance, which fastens via hook and loop (e.g., Velcro™) As noted above, the magnetic snap is detectable via a magnetometer integrated within the circuit components of the smart buckle to provide an indication of application of temperature therapy to the joint. In some embodiments, a magnetometer communicates with the processor of the smart buckle to provide a record of application of the temperature therapy appliance (e.g., hot pack or cold pack 885) to the patients body joint and the record may then in turn be transmitted to the patients computing device local to the wearable harness and which then in turn transmits patient telemetry data to the host organization. Such records indicating application of the cold or hot pack may be transmitted separately from or together with body joint positional data.

According to certain alternative embodiments, the ferrous stud may not be a magnet or magnetic, so as to not affect magnetometer of the smart buckle and thus not provide a false positive when temperature therapy appliance is not being used. In certain embodiments, the magnetic snap emits a signal via its associated magnetic field. In certain embodiments, the magnetic field of the magnetic snap extends sufficiently beyond the corresponding ferrous stud of the magnetic snap catch 265 (e.g., as a stray magnetic field) so as to signal the magnetometer of the smart buckle, thus indicating to the wearable harness that the magnetic snap 880 and temperature therapy appliance (e.g., cold pack/hot pack) are positioned in an operative and therapeutic location on the patient's body joint. In other embodiments, sensing of application of a temperature therapy appliance (e.g., cold pack/hot pack) may be determined by a thermal detector that may be included in the circuit components of the smart buckle. In other embodiments, the inertial sensors and magnetometer are incorporated together in a common package or chip, such as an "eCompass" brand chip available from Bosch Sensortec. Such components have been designed to detect the Earth's magnetic field and/or its direction, however, have been specially configured and repurposed to complement the described embodiments for use with detection of a local magnetic field as a sensor for operative detection of the presence of a component relative to magnetometer, that component being the magnetized stud affixed to a cold pack or a hot pack, such that presence of the cold pack or hot pack may be determined automatically by the embedded firmware of the wearable harness based on sensor data received from the magnetometer package or magnetometer sensor.

Figure 9B:
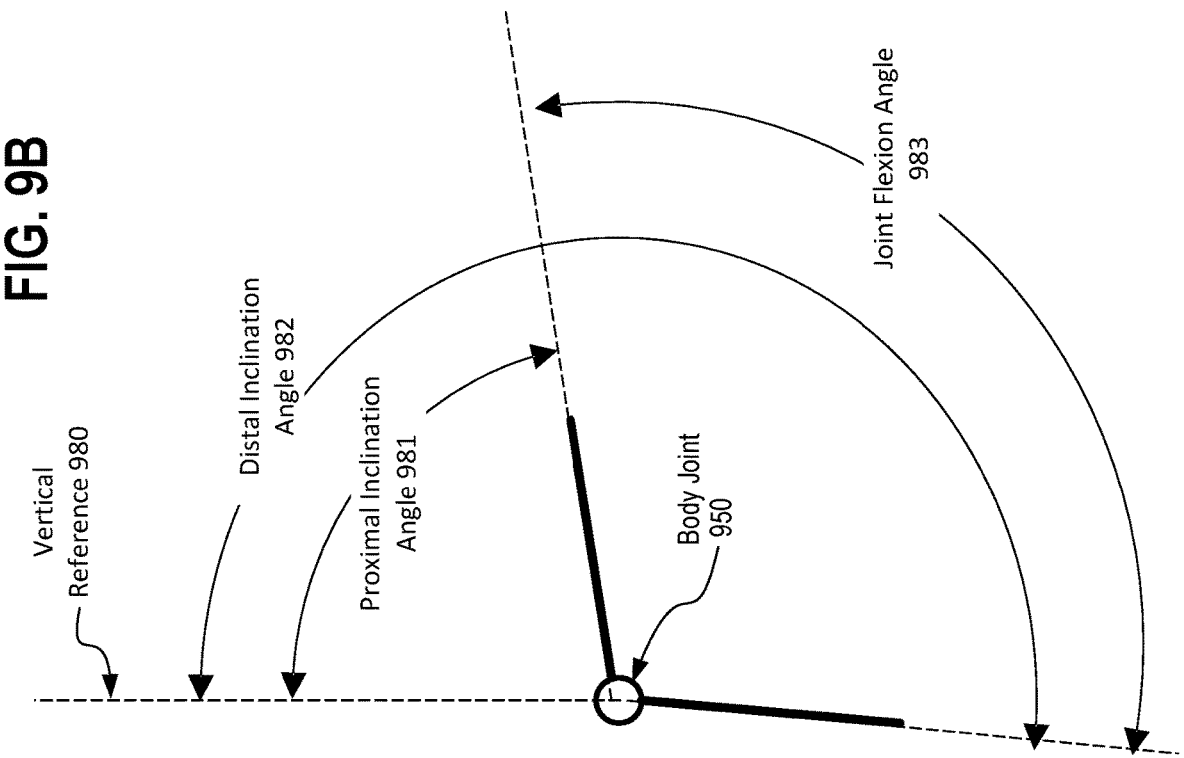
FIG. 9B illustrates determination of the static inclination angles, relative to vertical, of the body parts above (proximal to) and below (distal to) the joint of interest, as well as calculation of the flexion angle of the joint of interest by subtraction of the proximal inclination angle from the distal inclination angle, in accordance with described embodiments.
Figure 9A:
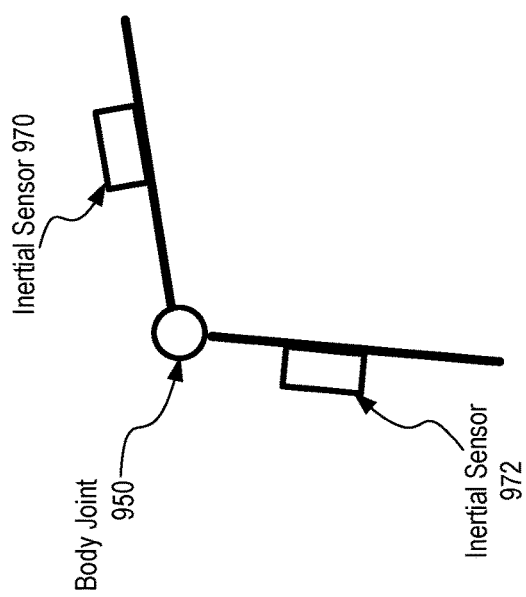
FIG. 9A is a schematic diagram illustrating a first inertial sensor and a second inertial sensor of wearable harness for use as a wearable joint rehabilitation device positioned at respective first and second body portions relative to a patient's body joint, in accordance with described embodiments.

FIG. 9A is a schematic diagram illustrating a first inertial sensor 970 and a second inertial sensor 972 of wearable harness for use as a wearable joint rehabilitation device positioned at respective first and second body portions relative to a patient's body joint 950, such as a patient's knee or elbow. For instance, the first inertial sensor 970 may be held proximal to the patient's knee by an upper or proximal strap whereas the second inertial sensor 972 may be held distal to the patient's knee by a lower or distal strap, thus positioning an inertial sensor both above and below or both proximal and distal to the body joint 950 of the patient via the wearable harness.

FIG. 9B illustrates determination of the static inclination angles, relative to vertical (via the vertical reference 980), of the body parts above (proximal to) and below (distal to) the patient's body joint 950 of interest, as well as calculation of the flexion angle 983 of the body joint 950 of interest by subtraction of the proximal inclination angle 981 from the distal inclination angle 982, each of which are derived from sensor data obtained by a processor of the patient wearable device from the first and second inertial sensors 970 and 972 positioned above and below or proximal and distal to the body joint 950 being monitored.

Figure 10:
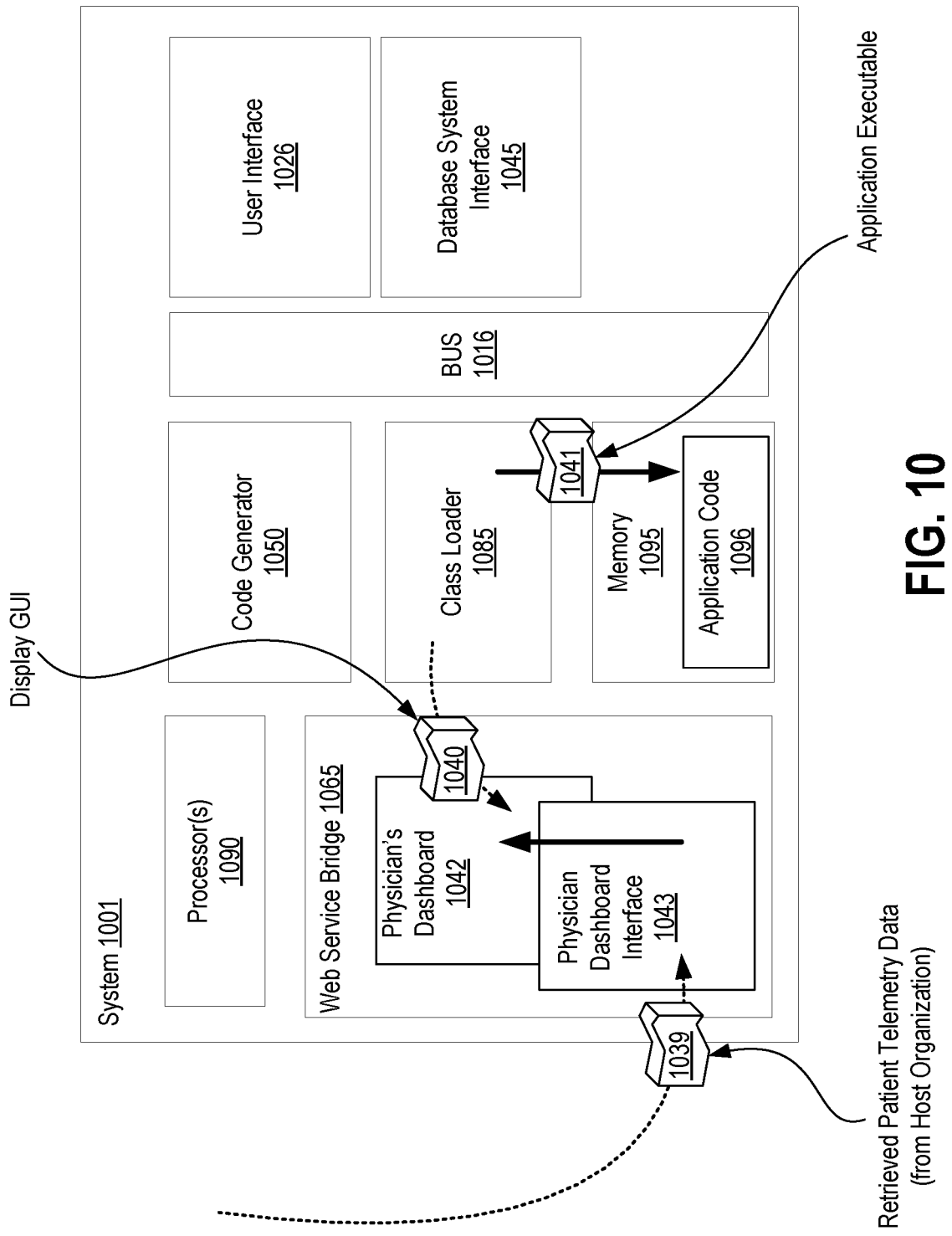
FIG. 10 shows a diagrammatic representation of a system within which embodiments may operate, be installed, integrated, or configured in accordance with described embodiments.

FIG. 10 shows a diagrammatic representation of a system 1001 within which embodiments may operate, be installed, integrated, or configured. In accordance with one embodiment, there is a system 1001 having at least a processor 1090 and a memory 1095 therein to execute implementing application code 1096. Such a system 1001 may communicatively interface with and cooperatively execute with the benefit of a hosted computing environment, such as a host organization, a remote database system or remote mass storage, an on-demand service provider, a cloud based service provider, a client-server environment, etc.

According to another embodiment of the system 1001, a user interface 1026 operates at a user client device remote from the system and communicatively interfaces with the system via a public Internet; in which the system operates at a host organization as a cloud based service provider to the user client device or operates on behalf of an external clinician computing device having an interface to a cloud based service provider. Such a cloud based service provider further implements a request interface exposed to the patient's computing device or the external clinician computing device via the public Internet, in which the request interface of the host organization receives inputs from the patient's computing device or the external clinician computing device to exchange and display patient telemetry data for those patients undergoing postoperative rehabilitation regimens prescribed by the clinician.

Bus 1016 interfaces the various components of the system 1001 amongst each other, with any other peripheral(s) of the system 1001, and with external components such as external network elements, other machines, client devices, cloud computing services, etc. Communications may further include communicating with external devices via a network interface over a LAN, WAN, or the public Internet.

Figure 11:
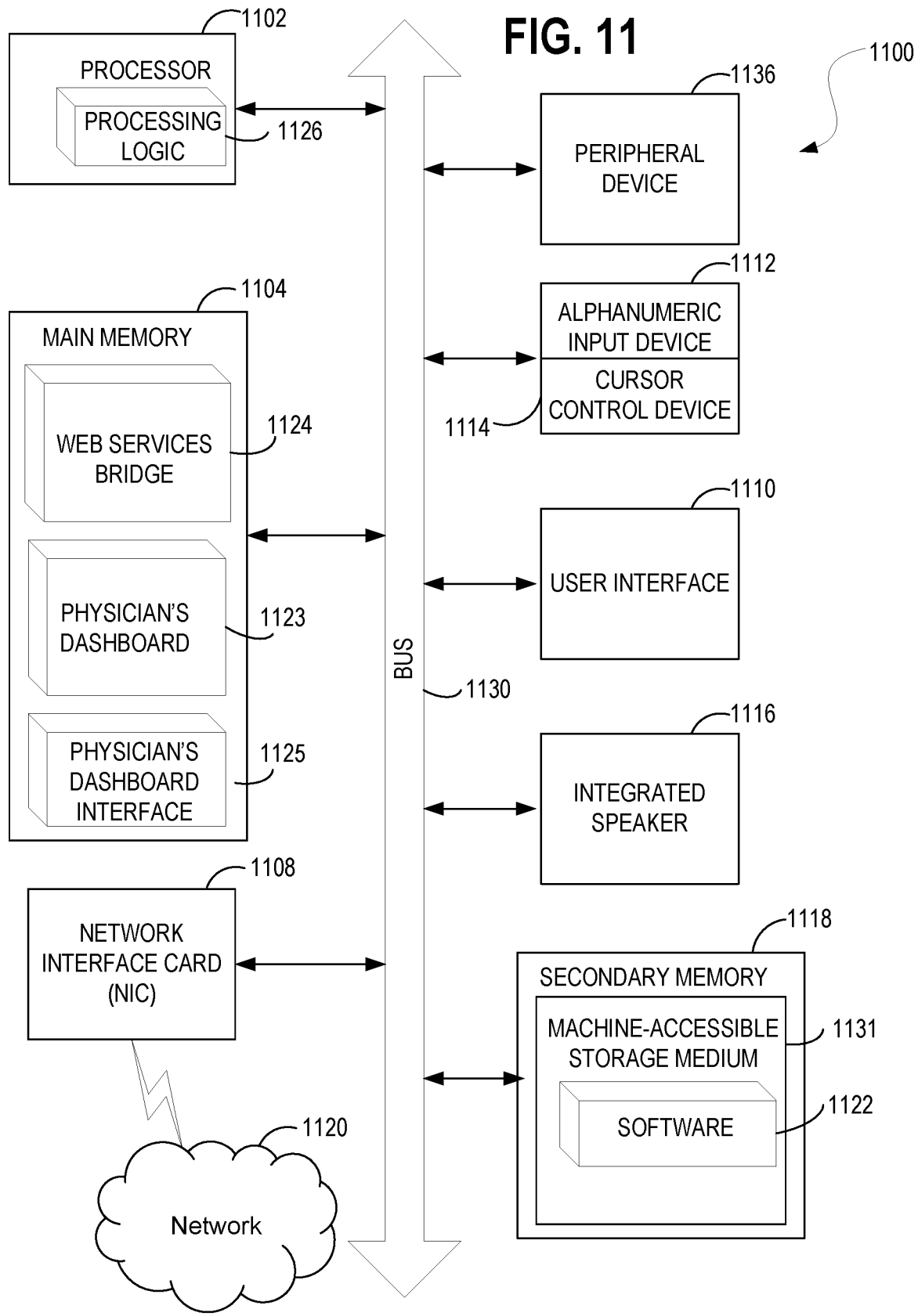
FIG. 11 illustrates a diagrammatic representation of a machine in the exemplary form of a computer system, in accordance with at least one embodiment.

FIG. 11 illustrates a diagrammatic representation of a machine 1100 in the exemplary form of a computer system, in accordance with one embodiment, within which a set of instructions, for causing the machine/computer system 1100 to perform any one or more of the methodologies discussed herein, may be executed. In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1100 includes a processor 1102, a main memory 1104 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 1118 (e.g., a persistent storage device including hard disk drives and a persistent database and/or a multi-tenant database implementation), which communicate with each other via a bus 1130. Main memory 1104 includes a web services bridge 1124 and a Physician's dashboard interface 1125 and a physician's dashboard 1123 via which the host organization is enabled to communicate, through the web services bridge 1124, with a patient's computing device or the external clinician computing device, so as to send, retrieve, synchronize, stream, or otherwise process and exchange patient telemetry data with the patient's computing device or the external clinician computing device and the respective patient application and physician's application (e.g., physician's dashboard) executing on such devices. Main memory 1104 and its sub-elements are operable in conjunction with processing logic 1126 and processor 1102 to perform the methodologies discussed herein.

Processor 1102 represents one or more general-purpose processing devices such as a microprocessor, central processing unit, or the like. More particularly, the processor 1102 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1102 may also be one or more special-purpose processing devices such as an application specific integrated circuit (ASIC), a field programmable gate array (FPGA), a digital signal processor (DSP), network processor, or the like. Processor 1102 is configured to execute the processing logic 1126 for performing the operations and functionality which is discussed herein.

The computer system 1100 may further include a network interface card 1108. The computer system 1100 also may include a user interface 1110 (such as a video display unit, a liquid crystal display, etc.), an alphanumeric input device 1112 (e.g., a keyboard), a cursor control device 1114 (e.g., a mouse), and a signal generation device 1116 (e.g., an integrated speaker). The computer system 1100 may further include peripheral device 1136 (e.g., wireless or wired communication devices, memory devices, storage devices, audio processing devices, video processing devices, etc.).

The secondary memory 1118 may include a non-transitory machine-readable storage medium or a non-transitory computer readable storage medium or a non-transitory machine-accessible storage medium 1131 on which is stored one or more sets of instructions (e.g., software 1122) embodying any one or more of the methodologies or functions described herein. The software 1122 may also reside, completely or at least partially, within the main memory 1104 and/or within the processor 1102 during execution thereof by the computer system 1100, the main memory 1104 and the processor 1102 also constituting machine-readable storage media. The software 1122 may further be transmitted or received over a network 1120 via the network interface card 1108.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims are to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A wearable apparatus for monitoring activity of a body joint, the wearable apparatus comprising:
   a wearable harness;
   wherein a first portion of the wearable harness comprises a proximal strap to be positioned proximal to the body joint;
   wherein a second portion of the wearable harness comprises a distal strap to be positioned distal to the body joint;
   a connecting section having a first end connected to the proximal strap and a second end connected to the distal strap;
   a first buckle housing fastened to the proximal strap of the wearable harness, the first buckle housing to be positioned proximal to the body joint via the proximal strap, wherein a switch on the first buckle housing is configured to determine whether the first buckle housing is in an open configuration or a closed configuration;
   a second buckle housing fastened to the distal strap of the wearable harness, the second buckle housing to be positioned distal to the body joint via the distal strap;
   integrated circuitry within the first buckle housing of the wearable harness, wherein the integrated circuitry of the first buckle housing includes at least a magnetometer and a first accelerometer;
   integrated circuitry within the second buckle housing of the wearable harness, wherein the integrated circuitry of the second buckle housing includes at least a second accelerometer;
   a memory and a microprocessor embedded within one of the first buckle housing or the second buckle housing, wherein the microprocessor is configured to collect and process sensor data received from the first accelerometer and the second accelerometer;
   a wireless transceiver embedded within one of the first buckle housing or the second buckle housing, wherein the wireless transceiver is configured to communicate patient telemetry data from the wearable apparatus to a remote computing device; and
   wherein the microprocessor is configured to periodically read configuration data from the switch on the first buckle housing to determine whether the first buckle housing is in the open configuration or the closed configuration, and upon determining the first buckle housing is in the closed configuration indicating the wearable apparatus is being worn by a patient, the microprocessor is configured to further sample data from the magnetometer to determine if a temperature therapy appliance is attached to the wearable apparatus based on detection of electromagnetic interference at the magnetometer emitted from a magnetic snap affixed to the temperature therapy appliance and magnetically affixed to a magnetic snap catch embedded within the first buckle housing.

2. The wearable apparatus of claim 1:
   wherein the wearable apparatus further comprises a switch embedded within the first buckle housing configured to determine whether the first buckle housing is in the open configuration or the closed configuration;
   wherein the wearable apparatus is placed into a no-power or a low power energy consumption state by a manufacturer or retailer prior to first use by a patient and wherein the wearable apparatus remains within the no-power or the low power energy consumption state while the switch on the first buckle housing remains within an open configuration; and
   wherein the wearable apparatus transitions out of the no-power or the low power energy consumption state and into a normal operating state upon activation of the switch embedded within the first buckle housing.

3. The wearable apparatus of claim 1:
   wherein the wearable apparatus further comprises a switch embedded within the first buckle housing;
   wherein the microprocessor is configured to periodically read configuration data from the switch to determine whether the first buckle housing is in the open configuration or the closed configuration; and
   wherein the microprocessor, upon determining the first buckle housing is in the closed configuration indicating the wearable apparatus is being worn by a patient, is further configured to initiate a sample period and to read data from the first accelerometer and the second accelerometer to determine (i) an angle for the sample period, and determine whether sample data read exceeds a threshold;
   when sample data does not exceed the threshold, the microprocessor is configured to iterate the sample period and to re-read the data from the first accelerometer and the second accelerometer until the sample data exceeds the threshold; and
   wherein the microprocessor is further configured to classify an activity after the sample data exceeds the threshold by classifying the sample data as one of walking, standing, sitting, elevating, or icing activities.

4. The wearable apparatus of claim 1:
wherein the microprocessor is configured to periodically measure a range of motion and to transmit instructions to a smartphone app executing on the remote computing device accessible to the patient and operating separate and remote from the wearable apparatus; and
wherein the instructions transmitted to the smartphone app are configurable within the smartphone app to coach the patient to undergo rehabilitation activities.

5. The wearable apparatus of claim 1:
wherein the wearable harness is positionable upon a patient's body at the body joint without occluding a surgical site of the patient.

6. The wearable apparatus of claim 5:
wherein the wearable harness comprises an open area between the proximal and distal straps and adjacent to the connecting section; and
wherein the open area is to be positioned over the surgical site of the patient to permit access to bandages, staples, stitches, or the scar at the patient's surgical site without requiring movement or removal of the wearable harness.

7. The wearable apparatus of claim 1:
wherein the proximal and distal straps maintain the first buckle housing and the second buckle housing in a consistent position relative to an axis of an underlying bone supporting the body joint.

8. The wearable apparatus of claim 7:
wherein the wearable harness is to be positioned upon a patient's knee body joint and wherein the proximal and distal straps maintain the first buckle housing and the second buckle housing in a consistent position relative to an axis of any or all of a femur, a tibia, and a fibula, of the patient, supporting the patient's knee body joint to maintain the wearable harness in a consistent orientation to the femur, the tibia, and the fibula bones of the patient; or alternatively
wherein the wearable harness is to be positioned upon an elbow body joint of the patient and wherein the proximal and distal straps maintain the first and the second buckle housings in a consistent position relative to an axis of any or all of a humerus, a radius, and an ulna bone or bones of the patient, supporting the elbow body joint of the patient to maintain the wearable harness in a consistent orientation to the humerus, the radius, and/or the ulna bone or bones of the patient.

9. The wearable apparatus of claim 1:
wherein the wearable harness is formed from a textile harness of flexible fabric with an underside at least partially coated by a non-slip silicone compound.

10. The wearable apparatus of claim 1:
wherein monitoring the activity of the body joint comprises the microprocessor being configured to monitor one or more of:
application of a temperature therapy appliance to the body joint;
application of a heat pack to the body joint;
application of an ice pack to the body joint;
movement of the body joint;
a range of motion of the body joint over time;
a maximum range of motion of the body joint;
prescribed exercises of the body joint; and
deviation from an expected trend for any of a range of motion of the body joint, a maximum range of motion of the body joint, or a duration of activity for the body joint.

11. The wearable apparatus of claim 1:
wherein the wearable harness forms a wearable joint rehabilitation device adaptable for use by a medical patient subsequent to a surgical procedure for the body joint or subsequent to injury of the body joint; and
wherein the wearable joint rehabilitation device operates in conjunction with a body joint rehabilitation regimen which captures movements of the patient into a cloud based computing environment based on information generated by sensor components locally integrated with the wearable joint rehabilitation device.

12. The wearable apparatus of claim 1:
wherein the wearable harness is configured to be positioned around a knee of the patient;
wherein the proximal strap is configured to be positioned above the knee of the patient and upon a thigh of the patient; and
wherein the distal strap is configured to be positioned below the knee of the patient and upon a calf of the patient.

13. The wearable apparatus of claim 1:
wherein the wearable harness is configured to be positioned around an elbow of the patient;
wherein the proximal strap is configured to be positioned above the elbow of the patient and upon a brachium pp of the patient; and
wherein the distal strap is configured to be positioned below the elbow of the patient and upon a forearm of the patient.

14. The wearable apparatus of claim 1:
wherein the wearable harness is configured to be positioned around a body joint of the patient selected from one of the following: an ankle, a shoulder, a wrist, and a hip joint;
wherein the proximal and the distal straps are configured to positioned on opposing sides proximal and distal, of the respective body joint of the patient; and
wherein the wearable harness is adapted to fit the shape of the respective selected one body joint of the patient.

15. The wearable apparatus of claim 1:
wherein the first and second buckle housings are interconnected via a wired interface traversing through the connecting section; and
wherein the first buckle housing comprises at least the microprocessor and a first inertial sensor;
wherein the second buckle housing comprises at least a second inertial sensor; and
wherein the microprocessor of the first buckle housing is configured to receive sensor data from the second initial sensor of the second buckle housing via the wired interface between the first and second buckle housings.

16. The wearable apparatus of claim 1:
wherein the integrated circuitry of the first buckle housing comprises:
an electronic compass implementing a combined function of both the magnetometer and the first accelerometer; and
wherein the microprocessor is further configured to receive sensor data from the electronic compass and configured to receive sensor data from the second accelerometer of the second buckle housing.

17. The wearable apparatus of claim 16:
wherein the microprocessor is configured to receive the sensor data from the first accelerometer and the second accelerometer by receiving one or more of: pitch orientation, roll orientation, yaw orientation, or azimuth orientation, relative to a bone of the patient, single axis inclination, dual axis inclination, linear acceleration, angular rate, and/or inertial measurement data.

18. The wearable apparatus of claim 1:
wherein the wireless transceiver embedded within one of the first buckle housing or the second buckle housing, is configured to transmit patient telemetry data to one of:
(i) a patient's computing device remote from the wearable apparatus, wherein the patient's computing device is configurable to forward the patient telemetry data to a remote cloud storage repository over a public Internet;
(ii) a clinician's computing device remote from the wearable apparatus, wherein the clinician's computing device is configurable to forward the patient telemetry data to the remote cloud storage repository over the public Internet; or
(iii) the remote cloud storage repository over the public Internet via digital or analog cellular transmission, wherein the remote cloud storage repository is configurable to transmit the patient telemetry data from the wearable apparatus to the remote cloud storage repository without traversing through either the patient's computing device or the clinician's computing device.

19. The wearable apparatus of claim 1:
wherein the wireless transceiver embedded within one of the first buckle housing or the second buckle housing comprises a Bluetooth protocol compliant wireless transceiver or a WiFi protocol compliant wireless transceiver, or both, configured to communicate patient telemetry data to a smartphone app executing on a patient's computing device or to a physician's dashboard application executing on a clinician's computing device, and wherein the patient telemetry data is forwarded to a remote cloud storage repository over a public Internet to be persistently stored.

20. A wearable apparatus for monitoring activity of a body joint, the wearable apparatus comprising:
a wearable harness;
wherein a first portion of the wearable harness comprises a proximal strap to be positioned proximal to the body joint;
wherein a second portion of the wearable harness comprises a distal strap to be positioned distal to the body joint;
a connecting section having a first end connected to the proximal strap and a second end connected to the distal strap;
a first buckle housing fastened to the proximal strap of the wearable harness, the first buckle housing to be positioned proximal to the body joint via the proximal strap, wherein a switch on the first buckle housing is configured to determine whether the first buckle housing is in the open configuration or the closed configuration;
a second buckle housing fastened to the distal strap of the wearable harness, the second buckle housing to be positioned distal to the body joint via the distal strap;
integrated circuitry within the first buckle housing of the wearable harness, wherein the integrated circuitry of the first buckle housing includes at least a magnetometer and a first accelerometer;
integrated circuitry within the second buckle housing of the wearable harness, wherein the integrated circuitry of the second buckle housing includes at least a second accelerometer;
a memory and a microprocessor embedded within one of the first buckle housing or the second buckle housing, wherein the microprocessor is configured to collect and process sensor data received from the first accelerometer and the second accelerometer;
a wireless transceiver embedded within one of the first buckle housing or the second buckle housing, wherein the wireless transceiver is configured to communicate patient telemetry data from the wearable apparatus to a remote computing device;
wherein the wearable apparatus is placed into a no-power or a low power energy consumption state by a manufacturer or retailer prior to first use by a patient and wherein the wearable apparatus remains within the no-power or the low power energy consumption state while the switch on the first buckle housing remains within the open configuration; and
wherein the wearable apparatus is configured to transition out of the no-power or the low power energy consumption state and into a normal operating state upon activation of the switch embedded within the first buckle housing.

21. A wearable apparatus for monitoring activity of a body joint, the wearable apparatus comprising:
a wearable harness;
wherein a first portion of the wearable harness comprises a proximal strap to be positioned proximal to the body joint;
wherein a second portion of the wearable harness comprises a distal strap to be positioned distal to the body joint;
a connecting section having a first end connected to the proximal strap and a second end connected to the distal strap;
a first buckle housing fastened to the proximal strap of the wearable harness, the first buckle housing to be positioned proximal to the body joint via the proximal strap;
a second buckle housing fastened to the distal strap of the wearable harness, the second buckle housing to be positioned distal to the body joint via the distal strap;
integrated circuitry within the first buckle housing of the wearable harness, wherein the integrated circuitry of the first buckle housing includes at least a magnetometer and a first accelerometer;
integrated circuitry within the second buckle housing of the wearable harness, wherein the integrated circuitry of the second buckle housing includes at least a second accelerometer;
a memory and a microprocessor embedded within one of the first buckle housing or the second buckle housing, wherein the microprocessor is configured to collect and process sensor data received from the first accelerometer and the second accelerometer;
a wireless transceiver embedded within one of the first buckle housing or the second buckle housing, wherein the wireless transceiver is configured to communicate patient telemetry data from the wearable apparatus to a remote computing device;
wherein the wearable apparatus further comprises a switch embedded within the first buckle housing and wherein the microprocessor is configured to periodically read configuration data from the switch to determine whether the first buckle housing is in the open configuration or the closed configuration;
wherein the microprocessor, upon determining the first buckle housing is in the closed configuration indicating the wearable apparatus is being worn by a patient, is configured to initiate a sample period and configured to read data from the first accelerometer and the second accelerometer to determine (i) an angle for the sample period and to further determine (ii) whether sample data read exceeds a threshold;

when sample data does not exceed the threshold, the microprocessor is configured to repeat the sample period and reading of the data from the first accelerometer and the second accelerometer until the sample data exceeds the threshold; and upon the microprocessor determining that the sample data exceeds the threshold, the microprocessor is further configured to classify an activity based on the sample data by classifying the sample data as one of walking, standing, sitting, elevating, or icing activities.

22. The wearable apparatus of claim 21:

wherein the microprocessor is configured to accumulate classified activities into daily statistics which log total time accumulated for each classified activity into the daily statistics;

wherein the wireless transceiver is configured to transmit the daily statistics to a remote source on-demand;

wherein the microprocessor is configured to further classify the icing activities based on the sample data; and wherein the microprocessor is configured to further accumulate icing activity duration and icing activity time of day into the daily statistics.

* * * * *